US010655167B2

(12) United States Patent
Heller et al.

(10) Patent No.: US 10,655,167 B2
(45) Date of Patent: *May 19, 2020

(54) LIGASE-ASSISTED NUCLEIC ACID CIRCULARIZATION AND AMPLIFICATION

(71) Applicant: GENERAL ELECTRIC COMPANY, Schenectady, NY (US)

(72) Inventors: Ryan Charles Heller, Amesbury, MA (US); Erik Leeming Kvam, Niskayuna, NY (US); John Richard Nelson, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 63 days.

This patent is subject to a terminal disclaimer.

(21) Appl. No.: 15/949,061

(22) Filed: Apr. 9, 2018

(65) Prior Publication Data

US 2018/0223349 A1    Aug. 9, 2018

Related U.S. Application Data

(63) Continuation of application No. 14/933,275, filed on Nov. 5, 2015, now Pat. No. 9,938,568, and a continuation-in-part of application No. 13/952,040, filed on Jul. 26, 2013, now Pat. No. 9,217,167, and a continuation-in-part of application No. 13/952,173, filed on Jul. 26, 2013, now Pat. No. 9,644,232.

(51) Int. Cl.
    C12P 19/34     (2006.01)
    C12Q 1/6844    (2018.01)
    C12Q 1/6869    (2018.01)

(52) U.S. Cl.
    CPC ......... *C12Q 1/6844* (2013.01); *C12Q 1/6869* (2013.01)

(58) Field of Classification Search
    CPC ............ C12Q 1/6844; C12Q 2521/501; C12Q 2525/179; C12Q 2531/125; C12Q 1/6869
    See application file for complete search history.

(56) References Cited

U.S. PATENT DOCUMENTS

| 9,644,232 B2 | 5/2017 | Kvam et al. | |
|---|---|---|---|
| 2002/0168645 A1* | 11/2002 | Taylor .................... | C12Q 1/682 435/6.12 |
| 2009/0130720 A1 | 5/2009 | Nelson et al. | |
| 2013/0143276 A1 | 6/2013 | Zhelkovsky et al. | |
| 2015/0031086 A1 | 1/2015 | Heller et al. | |

FOREIGN PATENT DOCUMENTS

| JP | 2006-512081 A | 4/2006 |
|---|---|---|
| JP | 2012-506704 A | 3/2012 |
| JP | 2012-080871 A | 4/2012 |
| WO | 2010094040 A1 | 8/2010 |

OTHER PUBLICATIONS

Machine Translation and Notification of Reasons for Refusal issued in connection with corresponding JP Application No. 2016-530068 dated May 8, 2018.
Nelson, et al., Methods and kits for reducing non-specific nucleic acid amplification, GE Co-Pending U.S. Appl. No. 61/599,119, filed Feb. 15, 2012.
Athanasios Tsaftaris et al, "Rolling Circle Amplication of Genomic Templates for Inverse PCR (RCA-GIP): a Method for 5' and 3'-Genome Walking Without Anchoring" Biotechnology Letters, Springer Netherlands, Dordrecht, vol. 32, No. 1, pp. 157-161 (Sep. 17, 2009).
EP Search Report for corresponding U.S. Appl. No. 15/949,061, dated Mar. 29, 2019; 8 pages.
Zhelkovsky, A.M., and Mcreynolds, L.A., "Simple and efficient synthesis of 5' preadenylated DNA using thermostable RNA ligase," Nucleic Acid Research, vol. 39, No. 17, pp. 1-6 (Jun. 30, 2011).
Machine Translation and First Office Action and Search issued in connection with corresponding CN Application No. 201480042259.0 dated Sep. 21, 2018.
Australian Examination Report for AU Application No. 2014292947 dated Oct. 31, 2019 (4 pages).
Anonymous, Enzyme Resource Guide. Cloning Enzymes from Promega, URL: https://www.promega.de/~/media/files/resources/product guides/cloning enzymes/cloningenz.pdf?la=en, (Nov. 11, 2014) [1], May 1, 1999, pp. 1-44.
Dean, F.B. et al., Rapid Amplification of Plasmid and Phage DNA Using Phi29 DNA Polymerase and Multiply-Primed Rolling Circle Amplification, Genome Research, Cold Spring Harbor Laboratory Press, Jun. 1, 2001, pp. 1095-1099, vol. 11, No. 6.
Anonymous, Biological Buffers, URL: https://www.applichem.com/fileadmin/Broschueren/BioBuffer.pdf, Jan. 1, 2008, pp. 1-20.
Nunez, A.N. et al., Application of Circular Ligase to Provide Template for Rolling Circle Amplification of Low Amounts of Fragmented DNA, 19th International Symposium on Human Identification, URL: http://www.promega.com/~/media/files/resources/conference%20proceedings/ishi%2019/oral%20presentations/nunez.pdf?la=en [1], Mar. 31, 2010, pp. 1-7.

(Continued)

*Primary Examiner* — Cynthia B Wilder
(74) *Attorney, Agent, or Firm* — Eversheds Sutherland (US) LLP

(57) ABSTRACT

Provided herein are methods for generation and amplification of a single-stranded DNA circle in a single reaction vessel from a linear DNA without any intervening purification steps. The single-stranded DNA circle is generated via a template-independent single-stranded DNA ligation. Whole-genome amplification of linear chromosomal DNA in a single tube using ligation-assisted DNA amplification is also provided.

16 Claims, 20 Drawing Sheets

(56) References Cited

OTHER PUBLICATIONS

Zhelkovsky, A.M., et al., Simple and Efficient Synthesis of 5' Pre-adenylated DNA Using Thermostable RNA Ligase, Nucleic Acids Research, Jun. 30, 2011, pp. e117-e117, vol. 39, No. 17.
Indian Examination Report for IN Application No. 201617000158 dated Dec. 19, 2019 (9 pages).
Tate et al., "Evaluation of Circular DNA Substrates for Whole Genome Amplification Prior to Forensic Analysis," Forensic Science International: Genetics, 2012, 6:185-190.
Imai et al., "A Simple and Rapid Method for Generating a Deletion by PCR," Nucleic Acids Research, 1991, 19(10):2785.

* cited by examiner

| Locus | Amlicon size (bp) | Genomic DNA | Plasma DNA | Circligase II-treated plasma DNA |
|---|---|---|---|---|
| mini CSF1PO | 89-129 | 22.26 | X | 25.55 |
| mini THO1 | 51-98 | 23.43 | X | 25.24 |
| mini TPOX | 65-101 | 24.62 | X | 23.92 |
| mini vWA | 88-148 | 21.29 | X | 20.66 |
| mini D5S818 | 81-117 | 22.14 | X | 26.19 |
| mini D7S820 | 136-176 | 23.46 | X | 27.11 |
| mini D8S1129 | 86-134 | 22.72 | X | 20.26 |
| mini D13S317 | 88-132 | 23.03 | 28.73 | 25.24 |
| mini D16S539 | 88-121 | 20.74 | 20.40 | 20.83 |
| mini D18S51 | 113-193 | 23.84 | X | X |
| Amelogenin | 106, 112 | 20.72 | 29.67 | 22.27 |
| D3S1358 | 99-147 | 20.13 | 20.77 | 20.85 |
| Total |  | 12/12 loci | 4/12 loci | 11/12 loci |

FIG. 5

|  | Fresh frozen-1 | Fresh frozen-2 | Rev10-1 | Rev10-2 | Rev11-1 | Rev11-2 | Rev12-1 | Rev12-2 |
|---|---|---|---|---|---|---|---|---|
| Expected # | 126 | 126 | 126 | 126 | 126 | 126 | 126 | 126 |
| Total # | 126 | 119 | 144 | 160 | 112 | 84 | 132 | 139 |
| True + | 126 | 119 | 36 | 53 | 40 | 43 | 86 | 71 |
| False + | 0 | 0 | 108 | 107 | 72 | 41 | 46 | 68 |
| False - | 0 | 7 | 90 | 73 | 86 | 83 | 40 | 55 |
| PPV | 1 | 1 | 0.25 | 0.33 | 0.36 | 0.51 | 0.65 | 0.51 |
| Sensitivity | 1 | 0.94 | 0.29 | 0.42 | 0.32 | 0.34 | 0.68 | 0.56 |

FIG. 19

LIGASE-ASSISTED NUCLEIC ACID CIRCULARIZATION AND AMPLIFICATION

FIELD OF INVENTION

The invention generally relates to methods for amplifying a linear nucleic acid sequence via rolling circle amplification in a single reaction vessel without any intervening isolation and/or purification steps. The methods involve generation of a single-stranded DNA circle from a single-stranded or double-stranded linear DNA via template-independent single-stranded DNA ligation, followed by rolling circle amplification using specialized primer sequences. The methods further relates to the whole genome amplification of a linear chromosomal DNA in a single reaction vessel via rolling circle amplification using a random primer mixture followed by its detection.

BACKGROUND

DNA amplification is a process of replicating a target double-stranded DNA (dsDNA) to generate multiple copies of it. Since individual strands of a dsDNA are antiparallel and complementary, each strand may serve as a template strand for the production of its complementary strand. The template strand is preserved as a whole or as a truncated portion and the complementary strand is assembled from deoxynucleoside triphosphates (dNTPs) by a DNA polymerase. The complementary strand synthesis proceeds in 5'→3' direction starting from the 3' terminal end of a primer sequence that is hybridized to the template strand.

Whole-genome amplification (WGA) involves non-specific amplification of a target DNA. WGA is often achieved by multiple displacement amplification (MDA) techniques employing random oligonucleotide primers for priming the DNA synthesis at multiple locations of the target DNA along with a high fidelity DNA polymerase having a strand displacing activity (e.g., Phi29 polymerase). Even though currently available commercial WGA systems such as GenomiPhi (GE Healthcare, USA) and RepliG (Qiagen) kits provide optimal results with high molecular weight target DNA, performance of these systems is poor when the target DNA is short and/or highly fragmented. When the target DNA is fragmented and the sequence length is less than about 1000 nucleotides, amplification of the target DNA using conventional methods results in decreased amplification speed, significant sequence dropout especially near the ends of the target DNA, and highly sequence-biased amplification. As the length of the template DNA is decreased, the likelihood of that strand being primed multiple times decreases in the MDA reaction. This decreases the amplification potential of these shorter fragments. Efficient methods for non-specifically amplifying short, fragmented DNA are therefore highly desirable.

Ligation-mediated polymerase chain reaction (PCR) has been used to amplify fragmented dsDNA. However, only a small fraction of the fragmented DNA gets amplified in these reactions leading to inadequate genome coverage. To efficiently amplify fragmented, target dsDNA, they may first be repaired and then be concatamerized by blunt-end ligation to generate sequences that are longer than 1000 base pairs (bp). However, a relatively higher concentration of the target DNA is often required to promote concatamerization and subsequent amplification. Circularization of double-stranded target DNA has also been employed in various nucleic acid based assays including MDA, WGA, hyperbranched rolling circle amplification (RCA) and massively parallel DNA sequencing. To effectively circularize and amplify fragmented dsDNA, the double-stranded ends of the fragmented DNA are first repaired, followed by blunt-end ligation to form double-stranded DNA circles. However, it is difficult to circularize double-stranded DNA fragments that are less than 500 bp in length.

The double-stranded DNA may be denatured to produce single-stranded DNA (ssDNA), which may further be circularized in a template-dependent intra-molecular ligation reaction using a ligase. However, prior sequence information of the target DNA is required to perform a template-dependent circularization. Template-independent intra-molecular ligation of ssDNA has also been documented. For example, TS2126 RNA ligase (commercially available under the trademarks THERMOPHAGE RNA ligase II or THERMOPHAGE ssDNA ligase (Prokaria, Matis, Iceland) or CIRCLIGASE ssDNA ligase (Epicenter Biotechnologies, Wisconsin, USA) has been used for making digital DNA balls, and/or locus-specific cleavage and amplification of DNA, such as genomic DNA. CIRCLIGASE I has a low degree (about 30%) of adenylation where as CIRCLIGASE II comprises a substantially adenylated form of TS2126 RNA ligase. Linear, single-stranded complementary DNA (cDNA) molecules prepared from 5'-end fragments of mRNA have also been amplified via rolling circle replication after circularization using TS2126 RNA ligase. By appropriately incorporating a sense RNA polymerase promoter sequence in to the cDNA, the circularized cDNA template has shown to act as a transcription substrate and thus effect the amplification of the mRNA molecules in a biological sample. Further, the TS2126 RNA ligase has been used for amplifying the cDNA ends for random amplification of cDNA ends (RACE). From limited amounts of fragmented DNA, DNA template for rolling circle amplification has also been generated by employing TS2126 RNA ligase. The method involved denaturing the linear, fragmented dsDNA to obtain linear ssDNA fragments, ligating the linear ssDNA with CIRCLIGASE ssDNA ligase to obtain single-stranded DNA circle, and then amplifying the single-stranded DNA circle using random primers and Phi29 DNA polymerase via RCA. However, even after optimizing the reaction conditions, the amount of generated single-stranded circular DNA was highly variable and sequence dependent. For example, oligonucleotides comprising a 5'G and a 3'T nucleotide ligated significantly better than its complementary oligonucleotide comprising a 5'A and a 3'C under identical ligation conditions. Further, intra-molecular ligation efficiency varied among linear ssDNA sequences having identical or very similar sizes but with small differences in nucleotide sequence. The efficiency also varied among linear ssDNA sequences of different sizes (e.g., sequence length ranging from 100 bases to kilobases in size). Moreover, all attempts of ligation-amplification reactions involved intermediate isolation, purification and/or cleaning steps, thus making the ligation-amplification workflow cumbersome. For example, analysis of forensic samples of fragmented DNA by circularization followed by rolling circle amplification was carried out in multiple steps comprising 5' DNA phosphorylation, adapter ligation, DNA circularization, and whole-genome amplification. Each step reactions were subjected to a reaction clean-up before performing the next step. Further, the multi-step process often resulted in the loss of template DNA and led to failed analysis. No amplification advantage was observed when ligation and amplification was performed in single reaction vessel; rather the components of the ligation reaction that were carried forward were often found to be inhibitory for the subsequent amplification reaction. Therefore, efficient methods for non-specifically amplifying short DNA sequences in a single reaction vessel without any intervening cleaning steps are highly desirable, especially in cases where representative and balanced whole genome information is desired. Further, methods for amplifying a linear nucleic acid sequence via rolling circle amplification in a single reaction vessel that overcome the inhibition caused by the reactants in each of the ligation-amplification are highly desirable.

BRIEF DESCRIPTION

In some embodiments, a method for amplification of a linear chromosomal DNA via rolling circle amplification is provided. The method comprises the steps of providing the linear chromosomal DNA, performing an intra-molecular ligation of the linear chromosomal DNA using a ligase that is capable of template-independent intra-molecular ligation of single-stranded DNA to generate a single-stranded DNA circle, and amplifying the single-stranded DNA circle via rolling circle amplification. The rolling circle amplification employs a random primer mixture that includes oligonucleotide sequences having at least one nucleotide analogue. All steps of the method, including the ligation reaction and the rolling circle amplification reaction, are performed in single reaction vessel without any intervening isolation or purification steps. The linear chromosomal DNA, if in double-stranded form, is denatured to generate single-stranded DNA prior to the intra-molecular ligation reaction. In some embodiments, the method is used for whole genome amplification of a target DNA.

DRAWINGS

These and other features, aspects and advantages of the invention will become better understood when the following detailed description is read with reference to the accompanying figures.

FIG. 5 illustrates the effectiveness of ligase-assisted whole-genome amplification for sensitive and balanced DNA amplification of twelve different CODIS loci.

Figure 18:
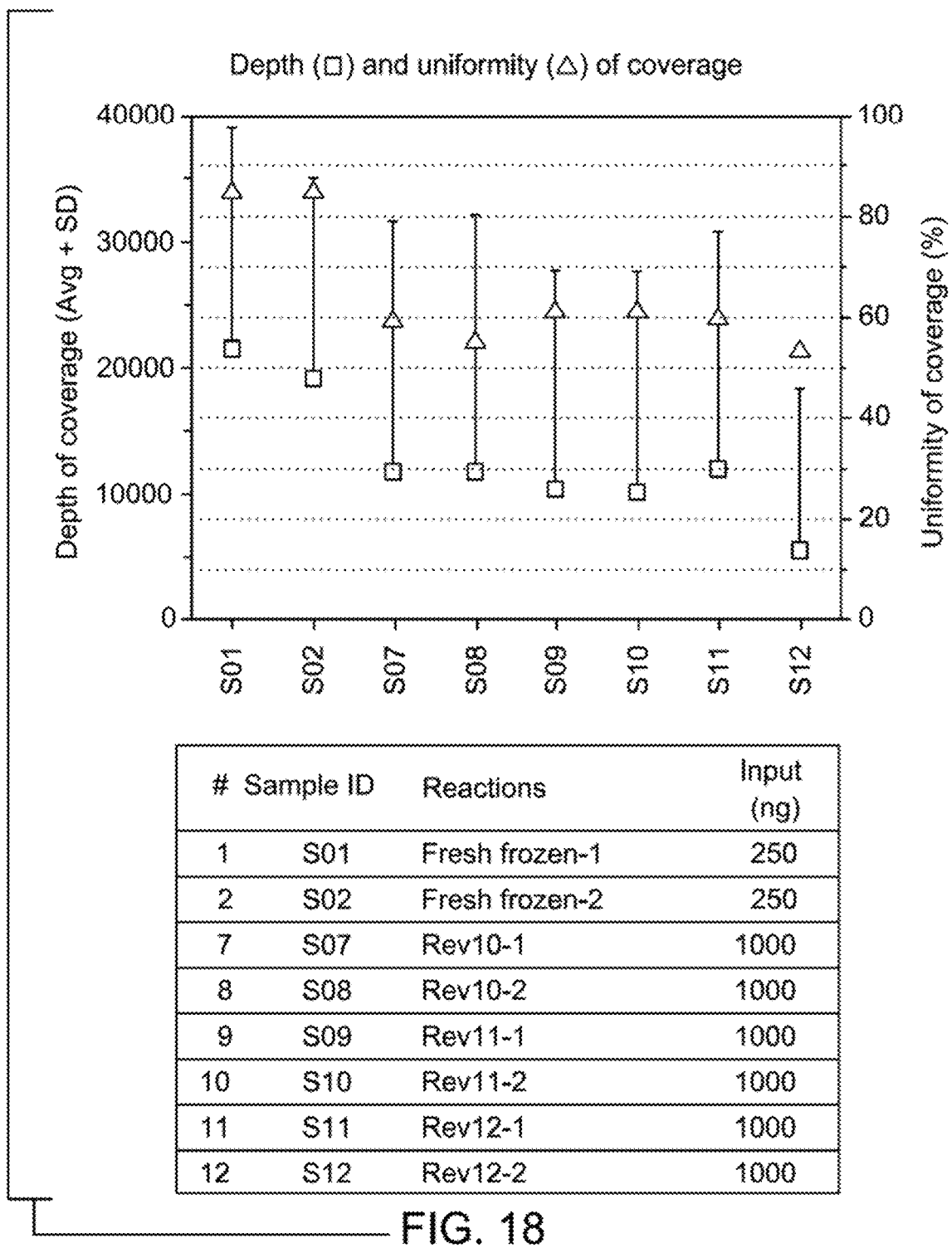

FIG. 18 illustrates the depth and uniformity of coverage when uracil DNA glycosylases (UDG) and formamidopyrimidine-DNA glycosylase (Fpg) was employed to repair/eliminate DNA damage from the single stranded DNA prior to the generation of single-stranded DNA circle or to repair/eliminate DNA damage from the generated single-stranded DNA circles, or when no DNA damage repair/elimination was performed.

FIG. 19 illustrates that better positive predictive value (PPV) and sensitivity when uracil DNA glycosylases (UDG) and formamidopyrimidine-DNA glycosylase (Fpg) was employed to repair/eliminate DNA damage from the single-stranded DNA circle prior to rolling circle amplification, or to repair/eliminate DNA damage from the generated single-stranded DNA circles, or when no DNA damage repair/elimination was performed.

DETAILED DESCRIPTION

The following detailed description is exemplary and not intended to limit the invention or uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between. To more clearly and concisely describe and point out the subject matter of the claimed invention, the following definitions are provided for specific terms, which are used in the following description and the appended claims.

As used herein, the term "nucleoside" refers to a glycosylamine compound wherein a nucleic acid base (nucleobase) is linked to a sugar moiety. A "nucleotide" refers to a nucleoside phosphate. A nucleotide may be represented using alphabetical letters (letter designation) corresponding to its nucleoside as described in Table 1. For example, A denotes adenosine (a nucleoside containing the nucleobase, adenine), C denotes cytidine, G denotes guanosine, U denotes uridine, and T denotes thymidine (5-methyl uridine). W denotes either A or T/U, and S denotes either G or C. N represents a random nucleoside and dNTP refers to deoxyribonucleoside triphosphate. N may be any of A, C, G, or T/U.

TABLE 1

Letter designations of various nucleotides.

| Symbol Letter | Nucleotide represented by the symbol Letter |
|---|---|
| G | G |
| A | A |
| T | T |
| c | c |
| u | u |
| R | G or A |
| y | T/U or C |
| M | A or C |
| K | G or T/U |
| s | G or C |
| w | A or T/U |
| H | A or C or T/U |
| B | G or T/U or C |
| v | G or C or A |
| D | G or A or T/U |
| N | G or A or T/U or C |
| (at N) | 2-amino dA or 2-thio-dT or G or C |

As used herein, the term "nucleotide analogue" refers to compounds that are structurally analogous to naturally occurring nucleotides. The nucleotide analogue may have an altered phosphate backbone, an altered sugar moiety, an altered nucleobase, or combinations thereof. Nucleotide analogues may be a natural nucleotide, a synthetic nucleotide, a modified nucleotide, or a surrogate replacement moiety (e.g., inosine). Generally, nucleotide analogues with altered nucleobases confer, among other things, different base pairing and base stacking proprieties. As used herein, the term "LNA (Locked Nucleic Acid) nucleotide" refers to a nucleotide analogue, wherein the sugar moiety of the nucleotide contains a bicyclic furanose unit locked in a ribonucleic acid (RNA)-mimicking sugar conformation. The structural change from a deoxyribonucleotide (or a ribonucleotide) to the LNA nucleotide is limited from a chemical perspective, namely the introduction of an additional linkage between carbon atoms at 2' position and 4' position (e.g., 2'-C, 4'-C-oxymethylene linkage; see, for example, Singh, S. K., et. al., Chem. Comm., 4, 455-456, 1998, or Koshkin, A. A., et. al., Tetrahedron, 54, 3607-3630, 1998). The 2' and 4' position of the furanose unit in the LNA nucleotide may be linked by an O-methylene (e.g., oxy-LNA: 2'-0, 4'-C-methylene-3-D-ribofuranosyl nucleotide), a S-methylene (thio-LNA), or a NH-methylene moiety (amino-LNA), and the like. Such linkages restrict the conformational freedom of the furanose ring. LNA oligonucleotides display enhanced hybridization affinity toward complementary single-stranded RNA, and complementary single-or double-stranded DNA. The LNA oligonucleotides may induce A-type (RNA-like) duplex conformations. Nucleotide analogues having altered phosphate-sugar backbone (e.g., PNA, LNA) often modify, among other things, the chain properties such as secondary structure formation. A star (*) sign preceding a letter designation denotes that the nucleotide designated by the letter is a phosphorothioate modified nucleotide. For example, *N represents a phosphorothioate modified random nucleotide. A plus (+) sign preceding a letter designation denotes that the nucleotide designated by the letter is a LNA nucleotide. For example, +A represents an adenosine LNA nucleotide, and +N represents a locked random nucleotide (i.e., a random LNA nucleotide). The letter designation "(at N)" represents a random nucleotide containing the nucleobases 2-amino dA, 2-tbio-dT, G or C.

As used herein, the term "oligonucleotide" refers to oligomers of nucleotides. The term "nucleic acid" as used herein refers to polymers of nucleotides. The term "sequence" as used herein refers to a nucleotide sequence of an oligonucleotide or a nucleic acid. Throughout the specification, whenever an oligonucleotide or nucleic acid is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide. The oligonucleotides or nucleic acids may be a DNA, an RNA, or their analogues (e.g., phosphorothioate analogue). The oligonucleotides or nucleic acids may also include modified bases and/or backbones (e.g., modified phosphate linkage or modified sugar moiety). Non-limiting examples of synthetic backbones that confer stability and/or other advantages to the nucleic acids may include phosphorothioate linkages, peptide nucleic acid, locked nucleic acid, xylose nucleic acid, or analogues thereof.

As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long.

As used herein, the term "random primer" refers to a mixture of primer sequences, generated by randomizing a nucleotide at any given location in an oligonucleotide sequence in such a way that the given location may consist of any of the possible nucleotides or their analogues (complete randomization). Thus the random primer is a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for whole-genome amplification reaction.

As described herein, the term "partially constrained primer" refers to a mixture of primer sequences, generated by completely randomizing some of the nucleotides of an oligonucleotide sequence (i.e., the nucleotide may be any of A, T/U, C, G, or their analogues) while restricting the complete randomization of some other nucleotides (i.e., the randomization of nucleotides at certain locations are to a lesser extent than the possible combinations A, T/U, C, G, or their analogues). For example, a partially constrained DNA hexamer primer represented by WNNNNN, represents a mixture of primer sequences wherein the 5' terminal nucleotide of all the sequences in the mixture is either A or T. Here, the 5' terminal nucleotide is constrained to two possible combinations (A or T) in contrast to the maximum four possible combinations (A, T, G or C) of a completely random DNA primer (NNNNNN). Suitable primer lengths of a partially constrained primer may be in the range of about 3 nucleotides long to about 15 nucleotides long.

As described herein, the term "partially constrained primer having a terminal mismatch primer-dimer structure" refers to a partially constrained primer sequence, wherein when two individual primer sequences in the partially constrained primer hybridize each other inter-molecularly, with an internal homology of three or more nucleotides, to form a primer-dimer structure having no recessed ends, or a primer-dimer structure having a single-nucleotide base 3' recessed ends, or a primer-dimer structure having a two-nucleotide base 3' recessed ends, there exists a nucleotide mismatch (i.e., nucleotides do not base-pair) at both the 3' terminal nucleotides in the primer-dimer structure. For example, a partially constrained pentamer primer represented by WNNNS provides a terminal mismatch at both the 3' terminal nucleotides when it is inter-molecularly hybridized to form a primer-dimer structure having no recessed ends. In the primer-dimer structure, there exists an internal homology of three nucleotides (i.e., the three random nucleotides in WNNNS may base-pair with each other when the primer-dimer structure having no recessed ends is formed by inter-molecular hybridization). However, this primer example does not provide a terminal mismatch when it is inter-molecularly hybridized to form a primer-dimer structure with single-nucleotide base 3' recessed ends. Similarly, a partially constrained hexamer primer represented by WWNNNS provides a terminal mismatch at both the 3' terminal nucleotides when it is inter-molecularly hybridized to form a primer-dimer structure having no recessed ends. Moreover, this primer example provides a terminal mismatch at both the 3' terminal nucleotides even when it is inter-molecularly hybridized to form a primer-dimer structure having a single-nucleotide base 3' recessed ends. A partially constrained heptamer primer represented by WWWNNNS provides a terminal mismatch at both the 3' terminal nucleotides when it is inter-molecularly hybridized to form a primer-dimer structure having no recessed ends. Further, this primer example provides a terminal mismatch at both the 3' terminal nucleotides when it is inter-molecularly hybridized to form a primer-dimer structure having a single-nucleotide base 3' recessed ends, or to form a primer-dimer structure having a two-nucleotide base 3' recessed ends.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase.

As used herein, multiple displacement amplification (MDA) refers to a nucleic acid amplification method, wherein the amplification involves the steps of annealing a primer to a denatured nucleic acid followed by a strand displacement nucleic acid synthesis. As nucleic acid is synthesized by strand displacement, a gradually increasing number of priming events occur, forming a network of hyper-branched nucleic acid structures. MDA is highly useful for whole-genome amplification for generating high-molecular weight DNA with limited sequence bias from a small amount of genomic DNA sample. Any strand displacing nucleic acid polymerase that has a strand displacement activity apart from its nucleic acid synthesis activity such as a Phi29 DNA polymerase or a large fragment of the Bst DNA polymerase may be used in MDA. MDA is often performed under isothermal reaction conditions, using random primers for achieving amplification with limited sequence bias.

As used herein, the term "pre-adenylated ligase" refers to a ligase that is in its adenylated form. The adenylated form of a ligase is capable of intra-molecular ligation of a linear, ssDNA molecule having a 5' phosphoryl group and a 3' hydroxyl group in the absence of ATP or dATP. A ligation using a pre-adenylated ligase refers to a ligation reaction wherein a high proportion of the ligase molecules that are used in the reaction are in their adenylated form. Generally more than 60% of the ligase molecules may be in their adenylated form. In some embodiments, when a ligation reaction is performed using a pre-adenylated ligase, more than 70% of the ligase molecules employed for the reaction may be in their adenylated form. In some other embodiments, when a ligation reaction is performed using a pre-adenylated ligase, more than 80%, 90%, or 95% of the ligase molecules employed for the reaction may be in their adenylated form.

As used herein the term "adenylating enzyme" refers to an enzyme that is capable of adenylating a nucleic sequence to generate a 5' adenylated nucleic acid. The 5'adenylated nucleic acid as used herein refers to a nucleic acid sequence that has a hydroxyl group at its 3' end and has adenylated terminal nucleotide at its 5' end. For example, a 5' adenylated DNA (AppDNA), refers to a DNA sequence that is adenylated at its 5' end and has a hydroxyl group at its 3' end.

As used herein the term "non-adenylated ligase" refers to a ligase that is in their non-adenylated form. The non-adenylated form of the ligase is capable of intra-molecular ligation of a linear, 5'-adenylated ssDNA molecule having a 3' hydroxyl group in the absence of ATP or dATP. A ligation using a non-adenylated ligase refers to a ligation reaction wherein a high proportion of the ligase molecules that are used in the reaction are in their non-adenylated form. Generally more than 60% of the ligase molecules may be in their non-adenylated form. In some embodiments, when a ligation reaction is performed using a non-adenylated ligase, more than 70% of the ligase molecules employed for the reaction may be in their un-adenylated form. In some other embodiments, when a ligation reaction is performed using a non-adenylated ligase, more than 80%, 90% or 95% of the ligase molecules employed for the reaction may be in their un-adenylated form.

As used herein, the term "melting temperature" ($T_m$) of a primer-template nucleic duplex refers to a temperature at which one-half of the duplex dissociates to single stranded molecules. The stability of a primer-template DNA duplex may be measured by its $T_m$. Primer length and sequence are critical determinants in designing the parameters of a successful amplification. The melting temperature of primer-template nucleic duplex increases with the primer length and with increasing GC content. Monovalent and divalent salt concentration (e.g., K+, $Mg_2$+, K+), temperature and presence of chemical denaturants can influence the Tm of a primer-template nucleic acid duplex and may be used to alter the stability of primer-template nucleic acid duplexes. For example, DNA duplex stability generally increases with higher salt concentrations, but decreases as a function of increased temperature or in the presence of denaturants. For example, high concentrations of salt (such as NaCl) raise the Tm of a primer-target DNA duplex since the Na+ ions can shield the negative charges on the phosphodiester backbones thereby reducing the electrostatic repulsion of DNA strands. On the other hand, higher temperatures (closer to or above the Tm of the primer-target DNA hybrid under the buffer conditions used) decreases duplex stability and DNA hybridization efficiency. The Tm of any defined sequence is dependent on the combined effects of duplex length, GC content, salt concentration, denaturant concentration, and buffer composition including pH. In addition, since hybridization is required during DNA amplification reactions, buffer compatibility with enzymatic activity is also a major concern. In order for optimal enzymatic activity, conditions for primer-template hybridization must not only be achieved, but also conditions for enzyme stability and enzymatic activity. In some cases, optimal enzyme activity may occur under conditions where primer-target hybridization is not optimal, and the inclusion of modifications to the primer composition that effect Tm may be used to improve primer-target hybridization by modifying the Tm of the duplex under those conditions used.

In some embodiments, a method for generating a single-stranded DNA circle from a linear DNA by incubating with a suitable ligase that is capable of template-independent intra-molecular ligation of a single-stranded DNA is provided. The linear DNA may be a linear chromosomal DNA, a cell-free circulating DNA, an ancient DNA or a DNA degraded by environmental exposure, or a formalin-fixed DNA. In some embodiments, the linear DNA may be a fragmented, linear DNA. The length of a fragmented, linear DNA may range from 15 nucleotides to 21000 nucleotides. The linear DNA may comprise sequences that already have ligatable terminal ends or it may comprise sequences that have non-ligatable terminal ends. In one embodiment, the linear DNA may comprise sequences that already have ligatable terminal ends. For example, the linear DNA may already have a phosphate group at the 5' terminal end and a hydroxyl group at the 3' terminal end. Such DNA sequences are amenable for intra-molecular ligation upon incubation with a suitable ligase. In some embodiments, a method for generating a single-stranded DNA circle from a linear chromosomal DNA is provided, wherein the method includes incubating the linear chromosomal DNA with a ligase that is capable of template-independent intra-molecular ligation of a single-stranded DNA to generate the single stranded DNA circle. In some embodiments, a pre-adenylated ligase is used for the ligation reaction. Any pre-adenylated ligase that is capable of ligating single-stranded DNA sequences in a template-independent manner may be employed. In some embodiments, a substantially adenylated form of TS2 126 RNA ligase is used for the template-independent intra-molecular ligation reaction. The linear chromosomal DNA, if in double-stranded form, needs to be denatured prior to the intra-molecular ligation reaction. The ligation reaction may be performed in the absence of ATP and/or dATP.

In some embodiments, the, linear DNA may comprise sequences that have non-ligatable terminal ends. For example, the linear DNA may have either a 5' hydroxyl group or a 3' phosphoryl group or both. In some embodiments, the method comprises the steps of providing a linear DNA, end-repairing the linear DNA by incubating it with a polynucleotide kinase (PNK) in the presence of a phosphate donor to generate a ligatable DNA sequence having a phosphate group at a 5' terminal end and a hydroxyl group at a 3' terminal end, and performing an intra-molecular ligation of the ligatable DNA sequence with a ligase to generate the single-stranded DNA circle. End repair may include phosphorylation of a 5' terminal nucleotide, de-phosphorylation of a 3' terminal nucleotide or both to generate the ligatable DNA sequence. The end-repaired, ligatable DNA, if in double-stranded form, needs to be denatured prior to the intra-molecular ligation reaction. In some embodiments, DNA is denatured prior to PNK reaction. Phosphorylation or de-phosphorylation of single-stranded DNA is generally more efficient than that of a double-stranded blunt or 5'-recessed ends. The phosphate donor and its concentration in the reaction mixture are selected such that it does not inhibit the subsequent intra-molecular ligation reaction. For example, any suitable phosphate donor other than adenosine triphosphate (ATP) or deoxyadenosine triphosphate (dATP) may be used for the end-repair reaction using PNK. Suitable phosphate donors include, but are not limited to, guanosine triphosphate (GTP), cytidine triphosphate (CTIP), uridine triphosphate (UTP) or dexoythymine triphosphate (dTTP). In some embodiments, a pre-adenylated ligase is used for the ligation reaction. Any pre-adenylated ligase that is capable of template-independent, single-stranded DNA sequences may be employed. In some embodiments, a substantially adenylated form of TS2126 RNA ligase is used for the template-independent, intra-molecular ligation reaction. The kinase reaction and the ligation reaction are performed in the absence of ATP and/or dATP. All the steps of the method are performed in single reaction vessel without any intervening isolation or purification steps. The individual steps of the methods may be performed simultaneously or in sequential manner without any intermediate purification or isolation steps. For example, PNK along with GTP may be added to a reaction vessel (e.g., eppendorf tube) containing a nucleic acid solution comprising the linear target DNA to facilitate the end-repair of the linear target DNA. Any PNK that has a 5' phosphorylation and a 3' phosphatase activity (e.g., T4 PNK) may be used for the end-repair reaction. A combination of PNKs each of which has 5' phosphorylation or a 3' phosphatase may also be used for the end-repair reaction. Once the kinase reaction is completed, a pre-adenylated ligase may be added to the same reaction vessel to facilitate the intra-molecular ligation reaction.

The linear DNA may be a double-stranded or single-stranded DNA of either natural or synthetic origin. The DNA may be obtained from a biological sample (e.g., a sample obtained from a biological subject) or discovered from unknown objects (e.g., DNA obtained during a forensic investigation) in vivo or in vitro. For example, it may be obtained from, but not limited to, bodily fluid (e.g., blood, blood plasma, serum, urine, milk, cerebrospinal fluid, pleural fluid, lymph, tear, sputum, saliva, stool, lung aspirate, throat or genital swabs), organs, tissues, cell cultures, cell fractions, sections (e.g., sectional portions of an organ or tissue) or cells isolated from the biological subject or from a particular region (e.g., a region containing diseased cells, or circulating tumor cells) of the biological subject. The biological sample that contains or suspected to contain the target linear DNA (i.e., linear DNA of interest) may be of eukaryotic origin, prokaryotic origin, viral origin or bacteriophage origin. For example, the target linear DNA may be obtained from an insect, a protozoa, a bird, a fish, a reptile, a mammal (e.g., rat, mouse, cow, dog, guinea pig, or rabbit), or a primate (e.g., chimpanzee or human). The linear DNA may be a genomic DNA (e.g., a linear chromosomal DNA) or a cDNA (complementary DNA). The cDNA may be generated from an RNA template (e.g., mRNA, ribosomal RNA) using a reverse transcriptase enzyme. The linear DNA may be a fragmented DNA and may have non-ligatable terminal nucleotides. For example, linear DNA may comprise a 5' hydroxyl group and/or a 3'phosphate group such that a DNA ligase cannot perform an intra-molecular ligation reaction. The linear DNA may be dispersed in solution or may be immobilized on a solid support, such as in blots, assays, arrays, glass slides, microtiter plates or ELISA plates. For example, the linear DNA may be immobilized on a substrate through a primer and then may be circularized and amplified.

When the linear DNA is in a double-stranded form, it needs be denatured to a single-stranded form prior to the intra-molecular ligation reaction. This may be achieved by using any of the art-recognized methods for the conversion of dsDNA to ssDNA sequences. For example, the dsDNA may be thermally denatured, chemically denatured, or both thermally and chemically denatured. The dsDNA may be chemically denatured using a denaturant (e.g., glycerol, ethylene glycol, formamide, urea or a combination thereof) that reduces the melting temperature of dsDNA. The denaturant may reduce the melting temperature by 5° C. to 6° C. for every 10% (vol./vol.) of the denaturant added to the reaction mixture. The denaturant or combination of denaturants (e.g., 10% glycerol and 6-7% ethylene glycol) may comprise 1%, 5%, 10%, 15%, 20%, or 25% of reaction mixture (vol./vol.). Salts that reduce hybridization stringency may be included in the reaction buffers at low concentrations to chemically denature the dsDNA at low temperatures. The dsDNA may be thermally denatured by heating the dsDNA, for example, at 95° C.

After the denaturing step, the generated ssDNA may be treated with a DNA or RNA ligase that is capable of intra-molecular ligation of ssDNA substrates in the absence of a template to form the single-stranded DNA circles. Suitable ligases that may be used for the ligation reaction include, but are not limited to, TS2126 RNA ligase, a T4 RNA ligase, T4 DNA ligase, T3 DNA ligase or *E. coli* DNA ligase. The conversion of linear, single-stranded DNA molecules to single-stranded DNA circles is conventionally performed via a template-dependent intra-molecular ligation reaction using a ligation enzyme such as T4 RNA ligase. However, template-dependent intra-molecular ligation of single-stranded DNA or single-stranded RNA has met only with limited success, particularly when the circularization of ssDNA molecules is to be performed in a population of ssDNA molecules of unknown sequence and/or size. Even though bacteriophage T4 RNA ligase I exhibits a template-independent intra-molecular ligation activity, this activity is far too low and inefficient for practical use in generating circular ssDNA molecules from linear ssDNA molecules.

In some embodiments, conversion of the ssDNA to single-stranded DNA circle is performed with a thermo-stable RNA ligase that has good template-independent, intra-molecular ligation activity for linear ssDNA and/or ssRNA substrates that have 5' phosphoryl and 3' hydroxyl groups. The ligase may be in a substantially pre-adenylated form. For example, TS2126 RNA ligase derived from the *Thermus* bacteriophage TS2126 that infects the thermophilic bacterium, *Thermus scotoductus* may be employed for template-independent circularization of the fragmented linear ssDNA to circular ssDNA_TS2126 RNA ligase is more thermostable (stable up to about 75° C.) than many of the mesophilic RNA ligases such as the T4 RNA ligase. The range of temperature for TS2126 RNA ligase activity can be greater than about 40° C., for example, from about 50° C. to about 75° C. Due to this, TS2126 RNA ligase may be used at higher temperatures, which further reduce undesirable secondary structures of ssDNA. The circularization of linear ssDNA may also be achieved by a ligase other than TS2126 RNA ligase or by employing any other enzyme having DNA joining activity such as topoisomerase. In some embodiments, the circularization of fragmented, single stranded DNA molecule is achieved by an RNA ligase 1 derived from thermophilic archeabacteria, *Methanobacterium thermoautotrophicum* (Mth RNA ligase) that has high template-independent ligase activity in circularizing linear, fragmented ssDNA molecules.

In some embodiments, a method for improving the efficiency of circularization of ssDNA by TS2126 RNA ligase is provided. Use of HEPES buffer having a pH of 8.0 for the ligation reaction increased the ligation efficiency. Template-independent ssDNA ligation was inefficient when the reaction was performed in TRIS buffer (e.g., For CIRCLIGASE II, the suggested 10× reaction buffer by EpiCenter comprises 0.33 M TRIS-Acetate (pH 7.5), 0.66 M potassium acetate, and 5 mM DTT). Further, manganese, an essential co-factor for the ligation reaction, is rapidly oxidized under alkaline conditions and forms a precipitate in the presence of TRIS. Air oxidation of $Mn^{2+}$ to $Mn^{3+}$ may be facilitated by the anions that can strongly complex the $Mn^{3+}$ ions. For example, when equal volumes of 0.2 mol/liter TRIS with pH appropriately adjusted with HCl and 2 mmol/liter $MnCl_2$ were mixed, the color change was immediate at pH 9.3 (the pH of TRIS base alone); had an initial time lag of about 3 minutes at pH 8.5; and was not detectable in 1 hour at pH values below 8.3. Although the reaction did not occur at lower pH, the changes observed at higher pH were not reversed by adding acid. Due to rapid oxidation of manganese in TRIS buffer, a higher concentration of manganese is essential for the ligation reaction (e.g., addition of $MnCl_2$ to a final concentration of 2.5 mM) when the intra-molecular ligation is performed in TRIS buffer. Further, it becomes difficult to accurately predict the working concentration of manganese in the reaction as the manganese concentration continues to decrease over time. Higher concentrations of manganese may lead to higher error-rate of the polymerase during amplification when the ligation and amplification is performed in a single reaction vessel. By substituting TRIS buffer with HEPES buffer in the ligation reaction, effective intra-molecular ligation may be achieved with manganese ion concentration less than 0.5 mM. Apart from HEPES, any of other the Good's buffers (see, for example, Good, Norman et al. Biochemistry, 5 (2): 467-477, 1966; and Good, Norman et al., Methods Enzymol., 24: 53-68, 1972) may be employed for the intra-molecular ligation reaction. In one embodiment, the intra-molecular ligation reaction is performed in 35 mM HEPES buffer (pH=8.0) containing about 2.5 mM $MnCl_2$, about 66 mM KOAc, about 0.5 mM DTT, about 0.003% (wt/wt) Tween-20 and about 0.5 M betaine.

The ssDNA circles in the ligation reaction mixture may be amplified under isothermal conditions via rolling circle amplification (RCA) methods. The amplification reagents including DNA polymerase, primers and dNTPs may be added to the same reaction vessel to produce an amplification reaction mixture and to initiate an RCA reaction. Individual reagents that are used for the amplification reaction may be pre-treated to remove any contaminating nucleic acids. The decontamination of the amplification reagents may be performed by employing any of the methods known in the art. For example, a decontaminated proof DNA polymerase such as decontaminated phi29 DNA polymerase may be used for the RCA reaction. The decontamination of a proof reading DNA may be performed by incubating it with a divalent cation in the absence of any dNTPs to remove the contaminating nucleic acids. The DNA polymerase that lacks proof reading capabilities such as Bst DNA polymerase may be used after incubating it with a proof reading DNA polymerase in presence of a divalent cation and in the absence of dNTPs to remove the contaminating nucleic acids. The decontamination may also be performed by incubating the amplification reagents with nucleases such as a DNAase. If the decontamination is performed by employing a nuclease, it needs to be removed or digested prior to the amplification reaction. The amplification reaction mixture may further include reagents such as single-stranded DNA binding proteins and/or suitable amplification reaction buffers. The amplification of ssDNA circles is performed in the same reaction vessel in which ligation is performed. Isolation or purification of the ssDNA circles and/or removal of the ligase is not necessary prior to the amplification reaction. The amplified DNA may be detected by any of the currently known methods for DNA detection.

RCA may be performed by using any of the DNA polymerases that are known in the art (e.g., a Phi29 DNA polymerase, a Bst DNA polymerase). It may be performed using a random primer mixture or by using a specific primer. In some embodiments, random primers are used for the RCA reaction. Primer sequences comprising one or more nucleotide analogues (e.g., LNA nucleotides, 2-Amino-dA, or 2-Tbio dT modification) may also be used. In some embodiments, nuclease-resistant primers (e.g., primer sequences comprising phosphorothioate groups at appropriate positions) are employed for the amplification reactions (e.g., NNNN*N*N). In some embodiments, RCA may be performed by contacting the ssDNA circles with a primer solution comprising a random primer mixture to form a nucleic acid template-primer complex; contacting the nucleic acid template-primer complex with a DNA polymerase and deoxyribonucleotide triphosphates; and amplifying the nucleic acid template. In some embodiments, the primer solution comprises a partially constrained primer such as WWNNS. The partially constrained primer may have a terminally mismatched primer-dimer structure. In some embodiments, a partially constrained primer that consists of a nucleotide sequence (W)x(N)y(S)z, wherein x, y and z are integer values independent of each other, and wherein value of x is 2 or 3, value of y is 2, 3 or 4, and value of z is 1 or 2 are used for the RCA reaction. The partially constrained primer may comprise one or more nucleotide analogues. In some embodiments, a nuclease-resistant, partially constrained primer comprising a modified nucleotide, and having terminal mismatch primer-dimer structure is employed for RCA reaction. Suitable primer sequences include, but are not limited to, +W+WNNS, W+W+NNS, +W+WNNNS, W+W+NNNS, W+W+NN*S, +W+WNN*S, W+W+NNN*S, +W+WNNN*S, W+W+N*N*S, +W+WN*N*S, W+W+NN*N*S, or +W+WNN*N*S. In some embodiments, RCA reaction is performed by contacting the ssDNA circle with a primer solution that consists essentially of a partially constrained primer mixture comprising a terminal mismatch primer-dimer structure and amplifying the ssDNA circle. In some other embodiments, RCA reaction is performed by contacting the ssDNA circle with a primer solution that consists essentially of a partially constrained primer mixture comprising a nucleotide analogue and amplifying the ssDNA circle. RCA of ssDNA circles produces large quantities of DNA with reduced sequence dropout and reduced amplification bias. The entire process of ssDNA ligation and amplification may be performed in a single tube without any intermediate purification or isolation steps. To avoid non-target amplification, the reagents used in ligation and/or nucleic acid amplification (e.g., primer solution, ligation buffers, DNA polymerase) may be pre-processed to remove any contaminating nucleic acids.

In some embodiments, a method amplification of a linear chromosomal DNA is provided. The method may be used for the whole genome amplification of a chromosomal DNA. The linear chromosomal DNA may be a cell-free circulating DNA, a DNA isolated from formalin-fixed paraffin-embedded sample, a forensic DNA sample, or an ancient DNA sample. The linear chromosomal DNA may have been exposed to environmental conditions and may be fragmented DNA. The method includes the steps of (a) providing the linear chromosomal DNA, (b) incubating the linear chromosomal DNA with a ligase that is capable of template-independent intra-molecular ligation of a single-stranded DNA sequence to generate a single-stranded DNA circle, and (c) amplifying the single-stranded DNA circle via rolling circle amplification using a random primer mixture to form an amplified DNA product. All steps of the method are performed in a single reaction vessel without any intervening isolation or purification steps. Individual reagents that are used for the amplification reaction may be pre-treated to remove any contaminating nucleic acids. The decontamination of the amplification reagents may be performed by employing any of the methods known in the art. For example, a decontaminated proof DNA polymerase such as decontaminated phi29 DNA polymerase may be used for the RCA reaction. The decontamination of a proof reading DNA may be performed by incubating it with a divalent cation in the absence of any dNTPs to remove the contaminating nucleic acids. The ligase may be a TS2126 RNA ligase, a T4 RNA ligase, a T4 DNA ligase, a T3 DNA ligase, an E. Coli DNA ligase or a combination of these. A pre-adenylated TS2126 RNA ligase is employed for the template-independent intra-molecular ligation of a single-stranded DNA sequence in an exemplary embodiment. The presence of excess salts, ligation reagents and/or other by-product may inhibit the rolling circle amplification of the generated single-stranded DNA circles when standard random primer mixture is used for RCA reaction. The random primer mixture used in the ligation-assisted whole genome amplification method in a single reaction vessel comprises oligonucleotide sequences comprising at least one nucleotide analogue. The nucleotide analogues in the random primer mixture are selected such that it increases a melting temperature (Tm) of the primer prevents primer-dimer formation and/or renders a primer resistant to nucleases. For example, in some embodiments, the method incorporates nucleotide analogues comprising modified nucleobase (e.g., 2-amino-dA) and LNAs that increase the melting temperature of the random primer mixture used for ligase-assisted whole genome amplification within a single reaction vessel. Inclusion of each 2-amino-dA base in a random hexamer primer mixture increases the Tm by up to approximately 3° C. and inclusion of each LNA nucleotide increases the Tm by 2-8° C. The modified random primer mixture may further comprise the nucleotide analogue comprising the nucleobase, 2-thio-deoxythymidine (2-thio-dT), wherein incorporation of the nucleotide analogues comprising 2-amino-dA and 2-thio-dT prevents primer-dimer formation. Further, the inclusion of nucleotide analogues comprising 2-amino-dA and 2-thio-dT improves the ability of the primer to hybridize to the target nucleic acid because 2-amino-dA forms three hydrogen bonds with an unmodified deoxythymidine (dT) and 2-thio-dT forms a normal stable pair with its unmodified partner (i.e., deoxyadenosine (dA)). The use of the modified nucleotide analogue bases and LNA nucleotides in the random primer mixture permits the use of more stringent hybridization buffers, thereby significantly reducing the formation of unwanted nucleic acid duplexes and decreasing the occurrence of unwanted non-target nucleic acid amplification. Moreover, high salt concentrations may also be used in the nucleic acid amplification reaction when the primer is a modified random primer. The random primer mixture is generally used in excess when compared to the target linear chromosomal DNA. The random primer mixture may be pre-treated with a nuclease such as a DNAse to remove any contaminating nucleic acids. In some embodiments, the linear chromosomal DNA is treated with a DNA repair enzyme prior to the ligation and amplification reaction. In some embodiments, the linear chromosomal DNA is treated with a DNA repair enzyme prior to the amplification reaction. In some embodiments the treatment with DNA repair enzyme is performed after the ligation reaction but prior to the amplification reaction. The treatment may be performed by incubating the ligation mixture with a uracil DNA glycosylase, a formamidopyrimidine-DNA glycosylase, or combinations thereof. Increased incubation time at higher temperatures such as conditions used for ligation with TS2126 RNA ligase risks greater incidents of spontaneous DNA base changes (e.g., DNA base transitions that lead to C-T and G-A mutations). In particular, single stranded DNA exhibits 140-fold faster spontaneous deamination kinetics than double-stranded DNA. For example, TS2126 RNA ligase-mediated circle sequencing illustrated that the treatment with DNA modification enzymes such as uracil DNA glycosylases (UDG) and/or formamidopyrimidine-DNA glycosylase (Fpg) effectively suppressed C-T and G-A mutations. In some embodiments, the individual steps of the methods are performed in a sequential manner without any intermediate purification or isolation steps. The steps of the method are generally performed in absence of adenosine triphosphate or deoxyadenosine triphosphate in a HEPES buffer. In one embodiment, the amplification reaction is performed in a buffer comprising about 38 mM HEPES (pH 8.0), about 18 mM MgCl$_2$, about 1 mM TCEP, about 2.5 mM KOAc, about −2.5% PEG-8000, about 0.007% Tween-20 and about 40 uM random primer mixture comprising oligonucleotide sequences having at least one nucleotide analogue. In some embodiments, all steps of the methods are performed simultaneously without any intermediate purification or isolation steps. While performing the ligation-assisted whole genome amplification in a single reaction vessel, the excess ligation reagents, excess DNA, excess salts and/or other impurities (e.g., undesired ligation products) from the ligation reaction may be present in the reaction vessel after ligation reaction, and the amplification reaction is performed in the same reaction vessel without removing any of these reagents, salts, DNA and/or other impurities. In a further embodiment, the linear chromosomal DNA is fragmented and may be treated with a polynucleotide kinase to generate a ligatable DNA prior to the ligation step. The PNK reaction is performed in presence of a phosphate donor other than adenosine triphosphate or deoxyadenosine triphosphate so that all the steps, including PNK reaction, intra-molecular ligation and RCA amplification may be performed in a single reaction vessel without any intervening isolation or purification steps.

In some embodiments, the random primer mixture comprises oligonucleotide sequences comprising at least one modified base. In some embodiments the modified base is either a 2-amino-deoxyadenosine (2-amino-dA) or 2-thio-deoxythymidine (2-thio-dT). In some other embodiments, random primer mixture comprises oligonucleotide sequences comprising at least one 2-thio-deoxythymidine and at least one 2-thio-deoxythymidine. In one example embodiment, the random primer mixture that is employed in the whole genome amplification comprises oligonucleotides that form Selective Binding Complimentary Oligonucleotides (SBC Oligonucleotides). SBC Oligonucleotides are complementary pairs of oligonucleotides that contain one or more modified base pairs (that is, each member oligonucleotides that forms the complementary pair are modified with a modified base). Each individual modified base does not form a stable base pair with its modified partner, but does form a particularly stable base pair with its natural (unmodified) counterpart. Thus, two complementary SBC oligonucleotides do not form a stable duplex with each other, but each individual SBC oligonucleotides does form a very stable duplex with an unmodified sequence such as a complementary target. This property enables an SBC duplex to effectively bind with both the sense and anti-sense strands of a DNA or RNA duplex target.

In one specific embodiment, the random primer mixture used in the whole genome amplification consists essentially of SBC Oligonucleotides. For example, one or more of deoxyadenosine in the oligonucleotide sequences in the random primer mixture may be replaced with 2-amino-deoxyadenosine and one or more of deoxythymidine in the oligonucleotide sequences in the random pruner mixture may be replaced with 2-thio-deoxythymidine to generate a primer mixture consisting essentially of selective binding complementary pairs. Incorporation of 2-amino-dA improves the ability of an oligonucleotide to hybridize to its target. The 2-amino-dA nucleotide base forms three hydrogen bonds (H-bonds) with thymine (T), compared with only two H-bonds between unmodified A and T. 2-Amino A:T base pairs thus have the same number of H-bonds as G:C base pairs do. Consequently, when a 2-amino-dA oligonucleotide binds to its unmodified target, the melting temperature ($T_m$) of the duplex is raised by up to about 3° C. per 2-amino-dA residue added, compared with the unmodified case. In addition, 2-amino-dA also destabilizes A-G wobble mismatches, presumably due to a steric clash between the 2-amino on A and the 2-amino on G. Thus 2-amino-dA modified oligonucleotides show better specificity for a target than their unmodified counterparts. An excellent pair of SBC oligonucleotides can be made by substituting 2-amino-dA for A, and 2-thio-dT for T (referred herein as AT random primer). Since 2-amino-dA only forms one hydrogen bond with 2-thio-dT, these modified base pairs are very weak, and the corresponding duplex is unstable. However, both 2-amino-dA and 2-thio-dT bind effectively with T and A bases, respectively. In general, SBC 20-mers annealed against a DNA 20-mer target exhibits Tm values 10° C. higher than the corresponding DNA-DNA hybrid, whereas the SBC-SBC hybrid exhibits Tm values 3° C. lower. The oligonucleotides in the AT random primer mixture may also comprise a phosphorothioate-modified nucleotide or an LNA nucleotide in addition to the 2-amino-dA and 2-thio-dT, which may further improve the melting temperature ($T_m$) of the primer-target duplex, prevent the formation of primer-dimer structures, and/or render the random primer mixture exonuclease-resistant.

Figure 14:
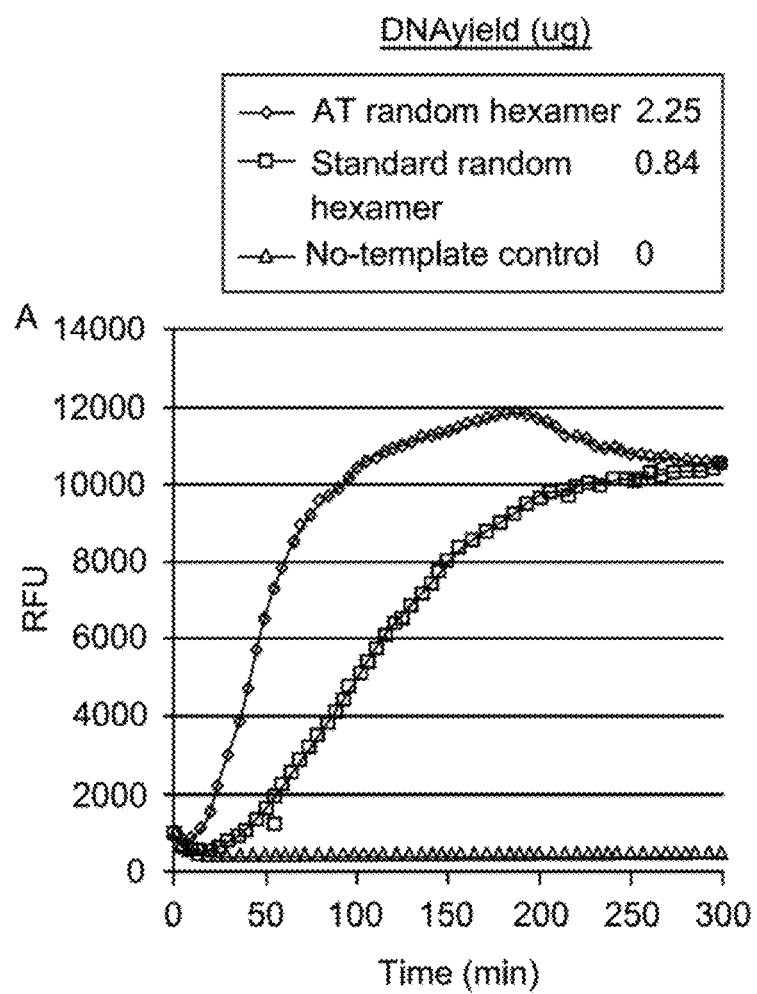
FIG. 14 illustrates a ligase-assisted whole-genome amplification of plasma DNA, using CIRCLIGASE II.

The single-tube amplification of the linear chromosomal DNA by ligation followed by RCA in a single reaction vessel without any intervening isolation and purification step was inefficient when standard nuclease-resistant random hexamers were employed (FIG. 14). The presence of excess salts, ligation reagents and/or other by-products inhibited the rolling circle amplification of the generated DNA circles. However, the usage of AT random primer mixture containing oligonucleotide sequences comprising 2-amino-dA, 2-thio-dT, phosphorothioate-modified nucleotides and LNA nucleotides surprisingly enables the ligation-amplification reaction to proceed in a single reaction vessel without any intervening isolation or purification steps. This primer enables the amplification reaction to perform under these buffer conditions better while the standard nuclease-resistant random hexamers fails to perform at the same level. The position of the LNA nucleotide in the primer sequence is chosen such that it does not occupy the 3' terminal end of the primer sequence. In some embodiments, each individual oligonucleotide sequence in the random primer mixture comprises at least one 2-amino-dA or 2-thio-dT In one exemplary embodiment, the ligase-assisted whole genome amplification via RCA in a single reaction vessel is performed using a random primer mixture comprising hexamer oligonucleotide sequences having a general structure, +N+N (atN)(atN)(atN)*N. The concentration of the random primer mixture is generally kept higher than the concentration of the single-stranded DNA circle during the above described whole genome amplification methods to promote multiple random-primed rolling circle amplification.

The amplified DNA product of the ligation-assisted whole genome amplification may be used to generate a genomic DNA library. The genomic library may be generated by fragmenting the amplified DNA product. In some embodiments, the fragmented product includes a single monomeric sequence of the concatameric amplified DNA product. In some other embodiments, the fragmented product includes more than one monomeric sequence of the concatameric amplified DNA product. The amplified DNA product may further be sequenced. Sequencing may be performed by employing any of the art-established techniques for DNA sequencing, including NextGen sequencing techniques. Since the amplified DNA product is a tandem repeat sequence of the DNA circle, the sequencing of the amplified DNA product may be used to eliminate the sequencing errors associated with the NextGen sequencing techniques. A major limitation of high-throughput DNA sequencing is the high rate of erroneous base calls produced. The generation of the genomic DNA library by whole genome amplification via ligation-assisted RCA amplification allows for robust downstream computational correction of the sequencing errors of the generated genomic DNA library. Since the linear chromosomal DNA templates are circularized, copied multiple times in tandem with a rolling circle polymerase, and then sequenced on any high-throughput sequencing machine, each read produced can be computationally processed to obtain a consensus sequence of all linked copies of the original sequence. Physically linking the copies ensures that each copy is independently derived from the original sequence and allow for efficient formation of consensus sequences in such circle sequencing protocols. The methods of whole genome amplification described herein thus allows a convenient protocol for single tube amplification of whole genome followed by error-free sequencing of the generated genomic DNA library. The genomic DNA library may also be used for hybridization-based capture of a target genomic DNA. The hybridization-based capture may either be performed in solution or in a surface (e.g., a microarray-based capture). The solution-based target capture is generally more scalable and economical especially when a large number of samples are involved. Further, the solution-based capture of a target DNA offers enhanced coverage uniformity. The captured target DNA may further be sequenced by targeted re-sequencing. The target DNA sequence may be selected to be an exome region of a genomic DNA to enable the exome sequencing.

In some embodiments, methods for amplification of limiting quantities of linear fragmented DNA via multiple displacement amplification (MDA) are provided. Conventional methods of MDA, when attempted on a linear fragmented DNA, result in decreased amplification speed and highly sequence-biased amplification. Moreover, significant sequence dropout is often observed particularly near the ends of the :fragmented DNA. To overcome these limitations, the :fragmented dsDNA is first converted to ssDNA. The ssDNA is then converted to single-stranded, circular DNA (i.e., DNA circle) via a template-independent intra-molecular ligation reaction, thereby eliminating the problematic DNA ends. Even ssDNA sequences that are shorter than 500 bp may be circularized using template-independent intra-molecular ligation of ssDNA. Further, no prior knowledge of the target sequence is needed to create DNA circles when the ligation of the ssDNA is performed in a template-independent manner. Prior to circularization, fragmented DNA may be treated with a PNK to repair the non-ligatable terminal ends. After circularization of the fragmented ssDNA, MDA is performed on the circularized DNA. The amplification reaction may be performed under isothermal conditions via employing rolling circle amplification (RCA) methods. RCA may be performed using commercially available RCA amplification kits such as TEMPLIPHI RCA kit (GE Healthcare). The TEMPLIPHI rolling-circle amplification employs locked nucleic acid-containing random primers, which provide higher sensitivity and amplification balance. In some embodiments, nuclease-resistant primers are used for RCA reaction. The methods disclosed herein improve amplification sensitivity, reduce sequence dropout and allow more balanced amplification. Since template-independent circularization of single-stranded fragmented DNA may be achieved on shorter sequences even at lower concentrations, a more balanced DNA amplification with faster kinetics and improved sequence coverage may be achieved when ligase-assisted whole-genome amplification is employed for amplification of highly fragmented DNA (e.g. circulating DNA in blood plasma). For example, the persistence length of ssDNA may be as low as 15 nucleotides for template-independent circularization of ssDNA. When CIRCLIGASE is employed for ligation reaction, under standard conditions, virtually no linear concatemers or circular concatemers are produced. Further, both the circularization and amplification reactions may be performed in a single reaction vessel without any intermediated purification or isolation steps thereby reducing the chances of contamination and simplifying the amplification workflow. Ligase-assisted whole-genome amplification methods may be employed for, but not limited to, analyzing circulating plasma cell-free DNA, fragmented DNA isolated from formalin fixed paraffin-embedded (FFPE) samples, forensics DNA samples that have been damaged by exposure to environmental conditions or ancient DNA samples. The amplified library may further be used for targeted detection of amplified sequences via qPCR or sequencing.

Various ligation-assisted whole-genome amplification methods described herein that comprise prior ligation of ssDNA fragments to DNA circles followed by rolling circle amplification, provide preferential amplification of a fragmented DNA over a high molecular weight genomic DNA. For example, plasma preparations comprising circulating DNA may often be contaminated with genomic DNA that are released from blood cells during the purification process. Conventional methods of whole-genome amplification via MDA amplify both the circulating DNA and the genomic DNA. In contrast, when fragmented, circulating DNA molecules are first circularized with TS2126 RNA followed by amplification of the circularized DNA molecules via RCA employing a Phi29 DNA polymerase the circulating DNA was preferentially amplified over the high molecular weight genomic DNA. Such preferential amplification of fragmented DNA over the genomic DNA is particularly suitable for diagnostic applications since diagnostically relevant DNA may be preferentially amplified for downstream analysis (see, Example 4). Further, ligase-assisted whole-genome amplification allows more robust amplification of fragmented DNA when compared to conventional MDA-based whole-genome amplification.

Figure 1:
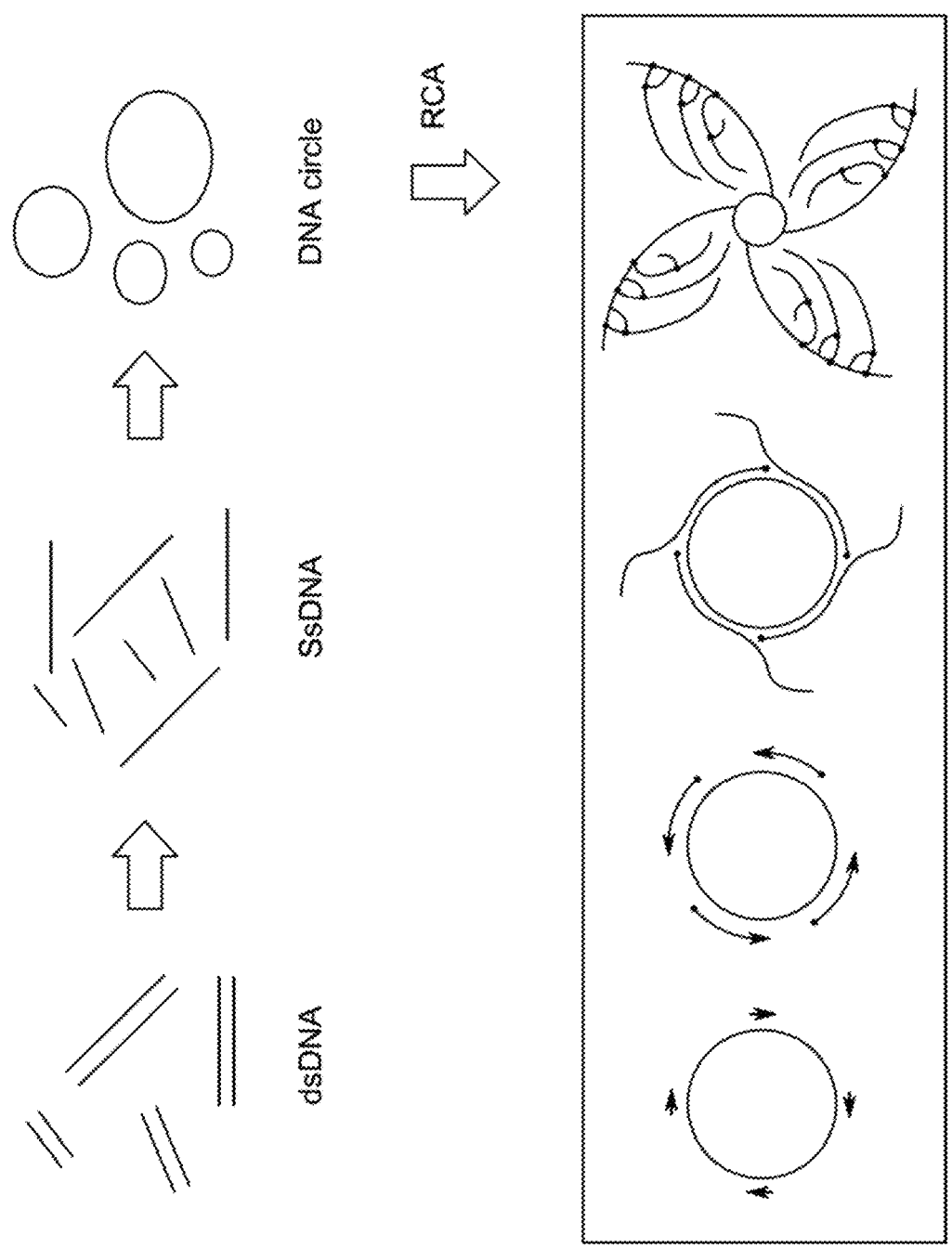
FIG. 1 illustrates a schematic representation of an embodiment of a ligase-assisted whole-genome amplification of a fragmented dsDNA.

FIG. 1 depicts a schematic representation of an embodiment of ligase-assisted whole-genome amplification of a fragmented dsDNA. The persistence length of double-stranded DNA is much higher (~150 bp) and its innate stiffness makes circularization of fragments less than 500 bp highly inefficient. Further, with small double-stranded fragmented DNA molecules of about 250 bp range, circularization is inefficient unless the ends are in proper alignment (~10.5 bp/turn). In contrast, the persistence length of the circularization of single-stranded fragmented DNA is very small, approximately 15 nucleotides, when compared to the double-stranded fragmented DNA. As depicted in FIG. 1, in ligase-assisted whole-genome amplification, fragmented dsDNA is first converted into single-stranded DNA circles. This may be achieved by incubating the fragmented double-stranded DNA at 95° C. for a sufficient period to denature the dsDNA into single strands. The fragmented ssDNA is then treated with a DNA or RNA ligase that is capable of template-independent, intra-molecular ligation of single-stranded DNA substrates to generate the single-stranded DNA circles. Non-limiting examples of ligases that may be used for intra-molecular ligation includes, CIRCLIGASE, T3 DNA ligase, T4 RNA ligase, Mth RNA ligase (MthRn11), or *E. coli* ligase. Amplification reagents, including DNA polymerase, random primers, and dNTPs are then added to initiate a RCA reaction on the single-stranded DNA circles. This ligase-assisted whole-genome amplification employing RCA produces large quantities of DNA with reduced sequence dropout and amplification bias in contrast to the conventional whole-genome amplification methods. Therefore, it may be used to amplify and detect even highly fragmented DNA. The entire process of generation of the single-stranded DNA circles and its subsequent amplification by RCA is done in a single tube without any intervening purification steps.

Figure 8:
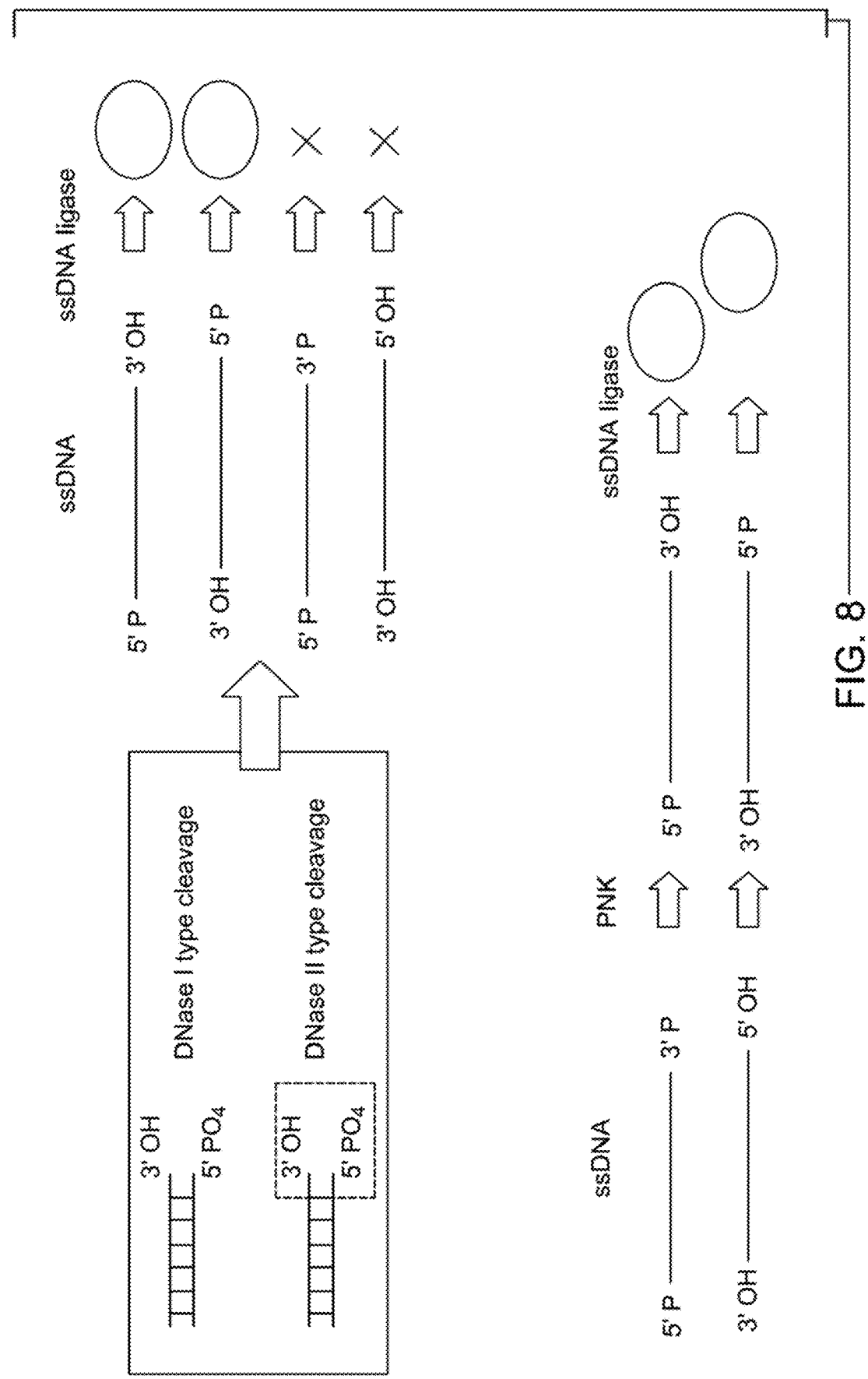
FIG. 8 illustrates a schematic representation of Rigase-assisted whole-genome amplification that includes the processing (e.g., end-repair) of a fragmented DNA using a polynucleotide kinase followed by ligase-assisted amplification of the processed fragmented DNA.

In some embodiments, a single-tube workflow is provided for ligase-assisted whole-genome amplification of fragmented DNA that includes processing of a fragmented DNA to repair the non-ligatable DNA ends. For example, if a fragmented single-stranded DNA does not contain a 5' phosphoryl group and a 3' hydroxyl group, it may not get ligated in an intra-molecular ligation reaction. Presence of such non-ligatable DNA sequences may cause an amplification bias in the ligase-assisted whole-genome amplification. For example, as schematically represented FIG. 8. DNA fragments that are generated by DNAse II digestion during cell death may contain a 5' hydroxyl group, a 3' phosphoryl group. The single-stranded DNA fragments originating from such double-stranded DNA fragments that contain a 5' hydroxyl group, a 3' phosphoryl group will not get circularized in an intra-molecular ligation reaction. Thus DNAse II type breaks are likely to be under-represented in whole-genome amplification. In some embodiments, the fragmented DNA is treated with a kinase (e.g., a T4 Polynucleotide Kinase, TPK) to phosphorylate the 5' hydroxyl groups and/or dephosphorylate the 3' phosphoryl group of the fragmented DNA. Inclusion of kinase in the reaction allows efficient circularization of fragments in a pool that do not contain a 5' phosphate. Phosphorylating the 5' ends of the fragmented DNA with a kinase followed by amplification of the fragmented DNA creates a more representative library.

Figure 9:
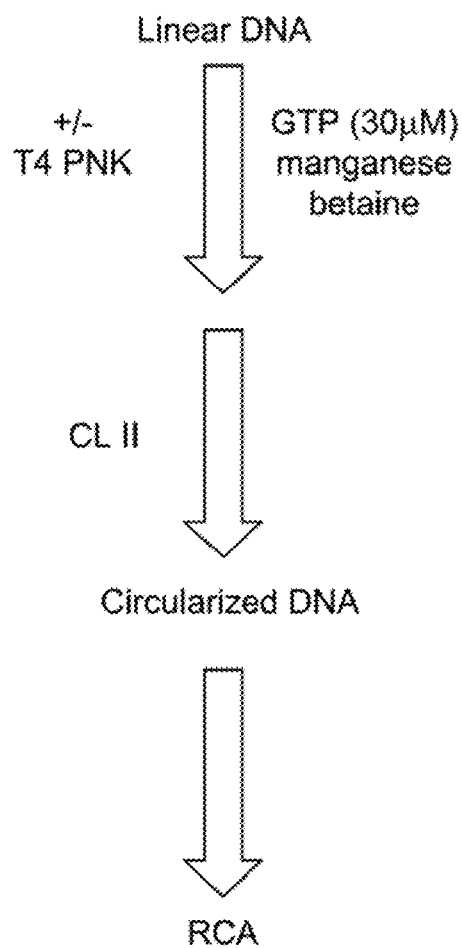
FIG. 9 illustrates a schematic representation of a single-tube reaction of ligase-assisted amplification of fragmented DNA employing PNK and CIRCLIGASE II in the presence of GTP.

In some embodiments, phosphorylation repair of the fragmented dsDNA may be performed by using a T4 PNK kinase. The phosphorylation repair may either be performed on the fragmented dsDNA or on the denatured fragmented ssDNA. If the phosphorylation repair is performed on the dsDNA, repaired dsDNA may then be denatured to linear ssDNA, which may be subsequently circularized using a CIRCLIGASE II (abbreviated as CLII). CIRCLIGASE II comprises a substantially adenylated form of TS2126 RNA ligase. Template-independent intra-molecular ligation of ssDNA by CIRCLIGASE II is inhibited by higher concentrations of ATP or dATP. However, the phosphorylation repair by kinase often requires the presence of ATP. Further, it may not be easy to remove ATP from the reaction mixture without damaging the DNA. For example, a phosphatase treatment of the reaction mixture to remove ATP will also result dephosphorylation of DNA (unless the DNA is protected, for example, by pre-adenylation), thus making the DNA strands un-ligatable. As a result, performing a phosphorylation repair of the fragmented DNA and generation of ssDNA circles in a single tube without any intervening purification or isolation steps is often difficult. The methods provided herein employ GTP, CTP, UTP or dTTP instead of ATP during the kinase reaction. Since CIRCLIGASE II is more tolerant to GTP or an alternate phosphate donor (e.g., CTP or UTP), the kinase repair step and the ligation step may be conducted in a single reaction vessel without any intervening purification and/or isolation steps. The kinase reaction mixture may further comprise additional reagents such as manganese salts and betaine (zwitterionic trimethylglycine). Once ligated, the ssDNA circles may be amplified. By conducting the ligation and amplification reaction at a relatively low concentration of GTP, the single-tube workflow described herein avoids the intermittent clean-up steps between enzymatic treatments and minimizes the DNA template loss (see FIG. 9 for a schematic representation a single-tube workflow involving kinase repair, ligation and amplification).

In some embodiments, an alternative method for generating a single-stranded DNA circle from a linear DNA is provided, wherein the method employs a DNA pre-adenylation step prior to intra-molecular ligation step. First, the linear DNA may be incubated with a polynucleotide kinase in the presence of ATP to generate a ligatable DNA sequence that comprises a phosphate group at 5' terminal end and a hydroxyl group at 3' terminal end. The ligatable DNA sequence is then incubated with an adenylating enzyme in presence of adenosine triphosphate to generate a 5' adenylated DNA sequence. The 5' adenylated DNA sequence has a free 3' hydroxyl group. The concentration of ATP is in the ligation reaction is selected such that no adenylation happens at the 3' end of the ligatable DNA sequence. The 5' adenylated DNA sequence is then incubated with a non-adenylated ligase, which is capable of template-independent intra-molecular ligation of the 5' adenylated DNA sequence, to generate the single-stranded DNA circle. If an ATP-dependent non-adenylated ligase is employed for the intra-molecular ligation reaction, the ATP may have to be removed from the reaction mixture by treating the reaction mixture with a phosphatase prior to the intra-molecular ligation reaction. The 5' phosphate at the terminal nucleotide of the DNA, which would normally be removed by a phosphatase, is protected from the phosphatase treatment because of the pre-adenylation. If the DNA is in double-stranded form, it needs to be denatured prior to intra-molecular ligation reaction. All the steps of the method are performed in single reaction vessel without any intervening isolation or purification steps.

In some embodiments, an RNA ligase such as RNA ligase derived from thermophilic archeabacteria, *Methanobacterium thermoautotrophicum* (Mth RNA ligase 1) is used in the presence of ATP to generate the adenylated form of the linear DNA. A mutant or suitably engineered ATP-independent ligase that is defective in self-adenylation, de-adenylation and/or adenylate transfer may be used for the intra-molecular ligation reaction of the adenylated linear DNA to generate the single-stranded DNA circle. For example, a motif V lysine mutant (K246A) of Mth RNA ligase may be employed. This mutant has full ligation activity with pre-adenylated substrates. Mth RNA ligase mutant that has an alanine substitution for the catalytic lysine in motif I (K97A) may also be employed. The activity of the K97A mutant is similar with either pre-adenylated RNA or single-stranded DNA (ssDNA) as donor substrates but has a two-fold preference for RNA as an acceptor substrate compared to ssDNA with an identical sequence. If ATP-dependent ligases such as TS2126 RNA ligase are employed for intra-molecular ligation reaction of the 5' adenylated DNA sequences, the ATP in the reaction may have to be removed prior to the ligation reaction.

In some embodiments, ligase-assisted whole-genome amplification employing the alternative workflow is provided. A schematic representation of this workflow is provided in FIG. 11. The method comprises the repair of fragmented DNA with a kinase and pre-adenylating the fragmented DNA at the 5' end with an RNA ligase or DNA ligase in presence of ATP prior to ligation and amplification. Fragmented DNA comprising sequences that have non-ligatable ends (e.g., sequences comprising 5' hydroxyl and/or 3' phosphoryl groups) are phosphorylated at 5' ends and de-phosphorylated at 3' ends by treating with a kinase to generate a ligatable DNA sequence. The ligatable DNA sequence may then adenylated using an RNA ligase such as Mth RNA ligase (MthRnl1), in the presence of ATP to generate an adenylated form of the fragmented DNA. The ATP is subsequently removed from the reaction mixture by treating the reaction mixture with a phosphatase (e.g., shrimp alkaline phosphatase (SAP)). Any method that is available in the art for 5' adenylation of a DNA may be employed (e.g., RNA ligase, DNA ligase or synthetic methods). The pre-adenylated single-stranded linear DNA is then treated with an RNA ligase that has a low degree of adenylation such as CIRCLIGASE I to generate DNA circles via intra-molecular ligation. The DNA circles are then amplified using RCA. In embodiments where CIRCLIGASE I to generated DNA circles via intra-molecular ligation, the intra-molecular DNA ligation and subsequent amplification reaction are performed in the absence of ATP. Elimination of ATP from the reaction mixture after kinase treatment and pre-adenylation reaction is essential since circularization of pre-adenylated ssDNA by CIRCLIGASE I is inhibited by ATP. In some embodiments, ATP is converted to adenosine and phosphate by treatment with a phosphatase. Even though adenosine is not inhibitory to the circularization reaction, the resultant phosphate may inhibit the intra-molecular ligation reaction. The generated phosphate may be further removed by treating the reaction mixture with phosphate-sequestering enzymes or with reagents that precipitate or remove phosphate (e.g., phosphate binding resin such as LayneRT resin) from the solution. Phosphate removal may also be achieved by treating the reaction mixture with an enzyme such as maltose phosphorylase which catalyzes conversion of maltose to glucose and glucose-I-phosphate, thereby removing the phosphate from the solution. Inclusion of kinase in the reaction allows circularization and amplification of DNA fragments in a pool that does not contain a 5' phosphate and/or 3' hydroxyl groups, thereby creating a more representative library via ligase-assisted amplification. Pre-adenylation of target DNA facilitates the use of ligases having low degree of adenylation (e.g., CIRCLIGASE I, which is about 30% adenylated) for intra-molecular ligation reaction. This may be of interest since ligases having high degree of adenylation (e.g., CIRCLIGASE II) ligate un-adenylated DNA only a single time. Thus, a stoichiometric amount of ligase is often required to drive an intra-molecular ligation reaction to completion. In contrast, ligases that have a low degree of adenylation (such as CIRCLIGASE I) have high turn-over, and can reversibly and catalytically or repeatedly act on multiple pre-adenylated DNA molecules. This increases ligation kinetics, reduces the quantity of ligase required, and potentially allows for increased circularization of more difficult or complex DNA templates.

In some embodiments, methods for ligase-assisted, whole-genome amplification is used for amplification and subsequent detection of circulating nucleic acids (e.g., circulating DNA from the non-cellular fraction of a biological sample) in a biological sample such as whole blood or urine. Circulating nucleic acids may originate from apoptotic or necrotic cells, or may be actively released from cells. Since cellular nucleases break down the high molecular weight genomic DNA into small, nucleosome-sized fragments, circulating nucleic acids are naturally highly fragmented. Highly fragmented circulating nucleic acid is often not amenable for conventional nucleic acid amplification methods. Further, circulating nucleic acids are present in very low quantities in the bloodstream. Standard rolling circle amplification (RCA) of double-stranded circulating linear nucleic acids is inefficient and highly biased. Separating the circulating nucleic acids to single-strands and circularizing with a ligase prior to rolling circle amplification improves efficiency and leads to less bias. To enable good RCA kinetics and high sensitivity with such dilute DNA template, in presence of excess ligation reagents, salts and other by-products of the ligation reaction, RCA methods employing primers comprising nucleotide analogues and/or LNAs are employed. This improved RCA has been optimized for trace DNA and single-cell amplification.

In some embodiments, a method of amplifying circulating DNA from the whole blood is provided. Circulating DNA is amplified from the non-cellular fraction of the whole blood (e.g., plasma or serum). This method comprises the steps of collecting the non-cellular fraction of the whole blood, collecting the circulating DNA (mostly presented in its native double-stranded form) from the non-cellular fraction, denaturing the double-stranded DNA to generate linear single-stranded DNA, circularizing the circulating single-stranded DNA molecule to generated single-stranded DNA circles, and amplifying the single-stranded DNA circles via rolling circle amplification. Due to persistence length, it is not generally possible to circularize dsDNA that has a sequence length smaller than 150 bp, and it is very difficult to circularize dsDNA until the DNA is longer than 200 bp. In contrast, linear ssDNA molecules having a sequence length of 15 nucleotides (nt) or more are very efficiently circularized by a suitable ligase as long as the 5' end is phosphorylated and the 3' end is hydroxylated. The circularization of the single-stranded DNA to generate single-stranded DNA circle is achieved by employing a ligase that is capable of template-independent intra-molecular ligation of single-stranded DNA. In some embodiments, the circularization of the single-stranded DNA molecules is performed by treating the single-stranded linear DNA with an RNA ligase such as CIRCLIGASE II.

In some embodiments, sensitivity of circulating DNA detection is further increased by phosphorylating the circulating nucleic acids with polynucleotide kinase (PNK) prior to the ssDNA ligation step and RCA. Upon incorporating the PNK step in the work flow, ligase-assisted whole-genome amplification methods presented herein could detect male circulating DNA in female whole blood when spiked at 1% levels (triplicate repeats). Template-independent intra-molecular ligation cannot be achieved unless the ssDNA template has a 5' phosphate group and a 3' hydroxyl group. A variety of conditions produce 5' hydroxyls in DNA (including DNase II enzymatic cleavage, and phosphatase activity in blood). The PNK treatment eliminates this problem and improves the diversity of rolling-circle amplified CNA library.

In some embodiments, kits for generation of a single-stranded DNA circle from a linear DNA are provided. In one embodiment, the kit comprises a polynucleotide kinase, a phosphate donor and a pre-adenylated ligase that is capable of template-independent, intra-molecular ligation of ssDNA sequence, packaged together. The polynucleotide kinase may be a T4 PNK. The phosphate donor may be chosen from GTP, UTP, CTP or dTTP. In one embodiment, the kit may include a TS2126 ligase. More than 60% of the TS2126 ligase may be pre-adenylated. The kit may further comprise buffers (e.g., HEPES), DNA amplification regents (e.g., DNA polymerase, primers, dNTPs) and other reagents (e.g., $MnCl_2$, betaine) that are employed for the generation of single-stranded DNA circle by the provided methods. In some embodiments, the kit may include a Phi29 DNA polymerase and random/partially constrained primers. In another embodiment, the kit comprises an adenylating enzyme, a phosphatase and a non-adenylated ligase packaged together. The kit may further comprise a polynucleotide kinase and/or a phosphate donor. The adenylating enzyme may be an RNA ligase I derived from *Methanobacterium thermoautotropicum* (Mth RNA ligase). The non-adenylated ligase may be a composition of TS2126 ligase, wherein more than 60% of the ligase is in the non-adenylated form. The kits may further include instruction for generation of single-stranded DNA circle from a linear DNA.

Practice of the invention will be still more fully understood from the following examples, which are presented herein for illustration only and should not be construed as limiting the scope of the present invention as defined by the appended claims. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "μL": microliters; "min.": minutes and "h.": hours.

EXAMPLES

Figure 2:
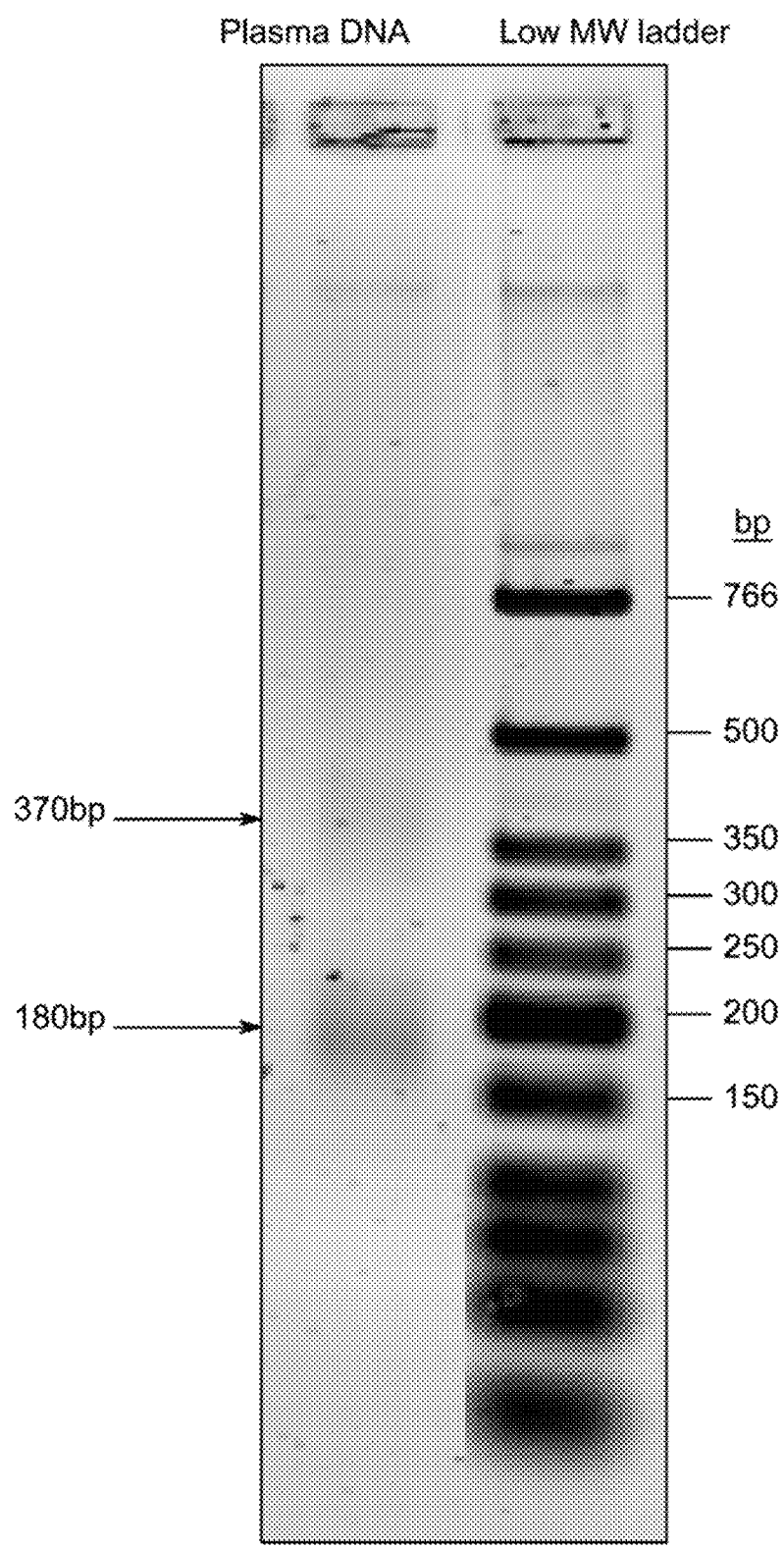
FIG. 2 illustrates size profiles of circulating DNA isolated from blood plasma of healthy individuals.

Example 1: Whole-Genome Amplification of Circulating Nucleic Acid from Blood Plasma Circulating DNA was isolated from citrate-phosphate-dextrose (CPD)—stabilized blood plasma of apparently healthy individuals using the Wako DNA extractor SP kit (Wako Pure Chemical Industries). Approximately 1.3 ng was analyzed by electrophoresis through a 2% agarose gel using TBE buffer, stained with SYBR Gold and visualized using a Typhoon imager. As depicted in FIG. 2, the majority of the circulating DNA was approximately 180 bp in length, with an additional smaller amount of sequences that were approximately 370 bp long, and a substantially smaller amount of higher molecular weight sequences.

350 pg circulating DNA from plasma was heated at 95° C. to denature the template. The denatured, single-stranded DNA template was then treated with an RNA or DNA ligase to generated single-stranded DNA circles. ATP-dependent T4 DNA ligase, cell-encoded NAD-dependent E. coli DNA ligase or a thermostable RNA ligase (CIRCLIGASE II) was used for the ligation reaction. 100 pg of DNA ligated single-stranded DNA circles were then subjected to whole-genome amplification using GenomiPhi kit (GE Healthcare) employing a Phi29 DNA polymerase. The amplification was performed using the primer mixture+N+N(at N)(at N)(at N)*N where the "(at N)" represents a random mixture containing 2-amino dA, 2-thio-dT, normal G and normal C. Real-time amplification was performed by adding a small amount of SYBR green I to the amplification mixture and monitoring the fluorescence signal increase over time in a Tecan plate reader (Tecan SNiPer, Amersham-Pharmacia Biotech). For comparison, an equivalent concentration of un-treated genomic DNA, untreated plasma DNA, and a sample without DNA template (No template amplification) were included.

Figure 3A:
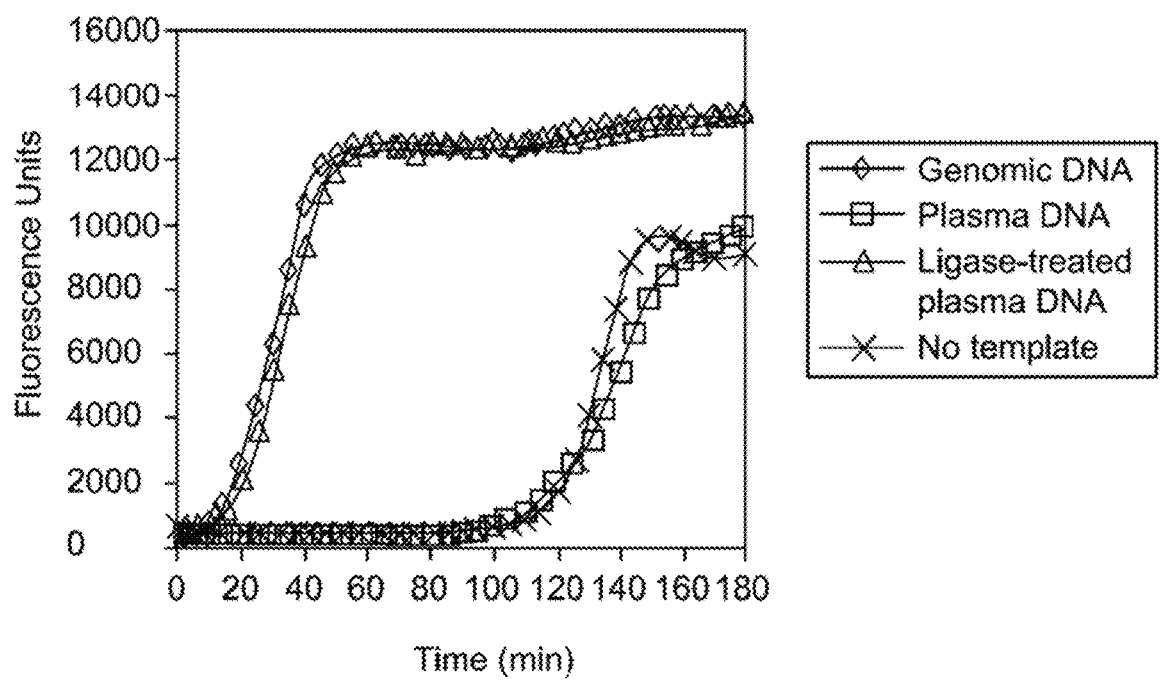
FIG. 3A illustrates a ligase-assisted whole-genome amplification of circulating DNA extracted from the non-cellular fraction of whole blood, using CIRCLIGASE II.
Figure 3B:
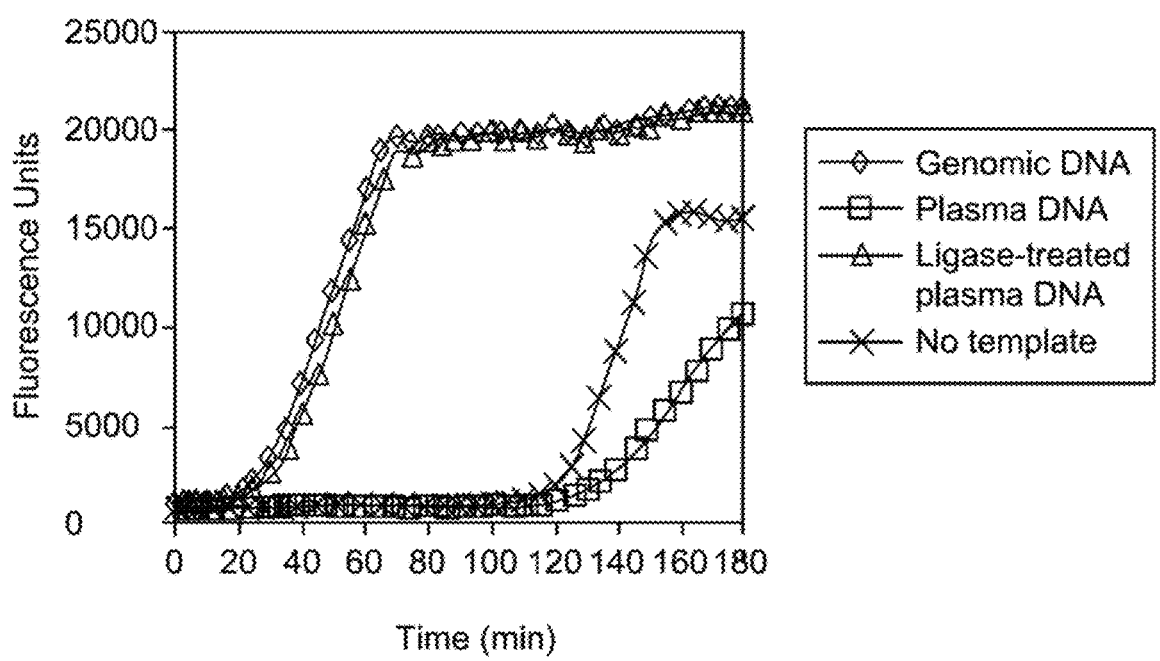
FIG. 3B illustrates a ligase-assisted whole-genome amplification of circulating DNA extracted from the non-cellular fraction of whole blood, using T4 DNA ligase.
Figure 3C:
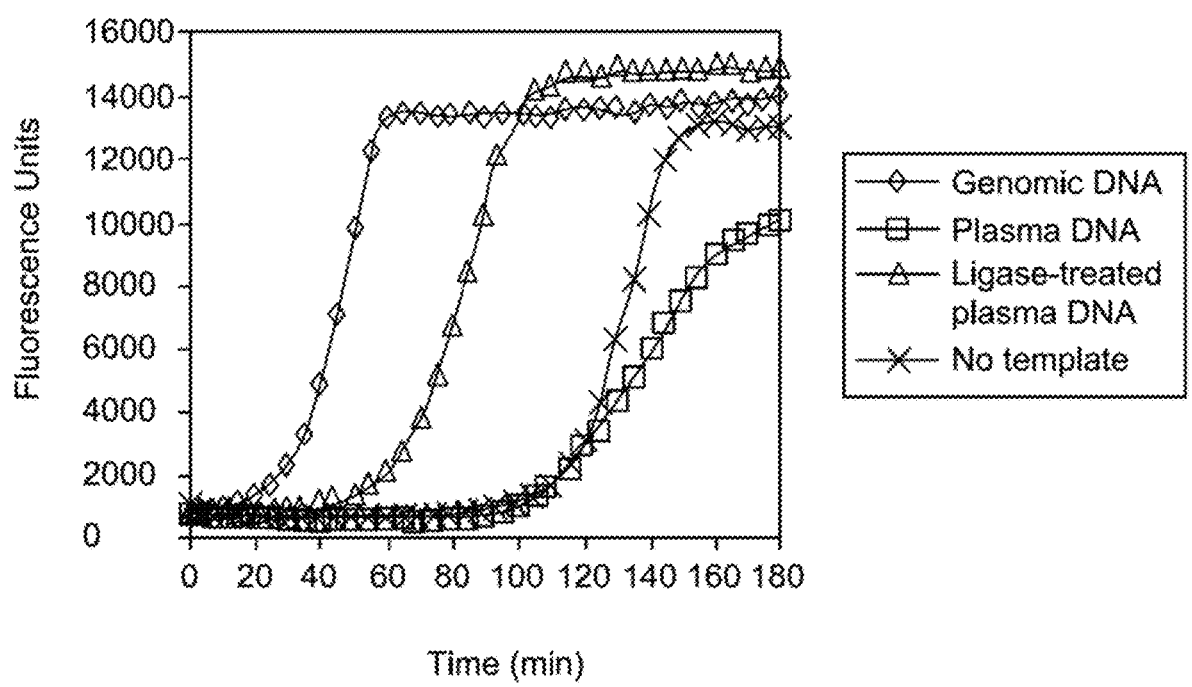
FIG. 3C illustrates a ligase-assisted whole-genome amplification of circulating DNA extracted from the non-cellular fraction of whole blood, using *E. Coli* DNA ligase.

As depicted in FIG. 3, the amplification kinetics of the untreated, fragmented plasma DNA were much lower when compared to an equivalent amount of high molecular weight genomic DNA, indicating a defect in amplification. However, when the fragmented plasma DNA was pre-treated and converted to single-stranded DNA circles using the CIRCLIGASE II, rapid amplification kinetics were achieved (FIG. 3A). The ligases, including the ATP-dependent T4 DNA ligase (FIG. 3B) and the cell-encoded NAD-dependent E. coli DNA ligase (FIG. 3C) were also effective, but with less efficiency, in restoring amplification kinetics of the fragmented plasma DNA. In these examples, the relative increase in amplification kinetics indicates the effectiveness of each of the ligases in promoting the intra-molecular ligation of the single-stranded DNA template.

Figure 4:
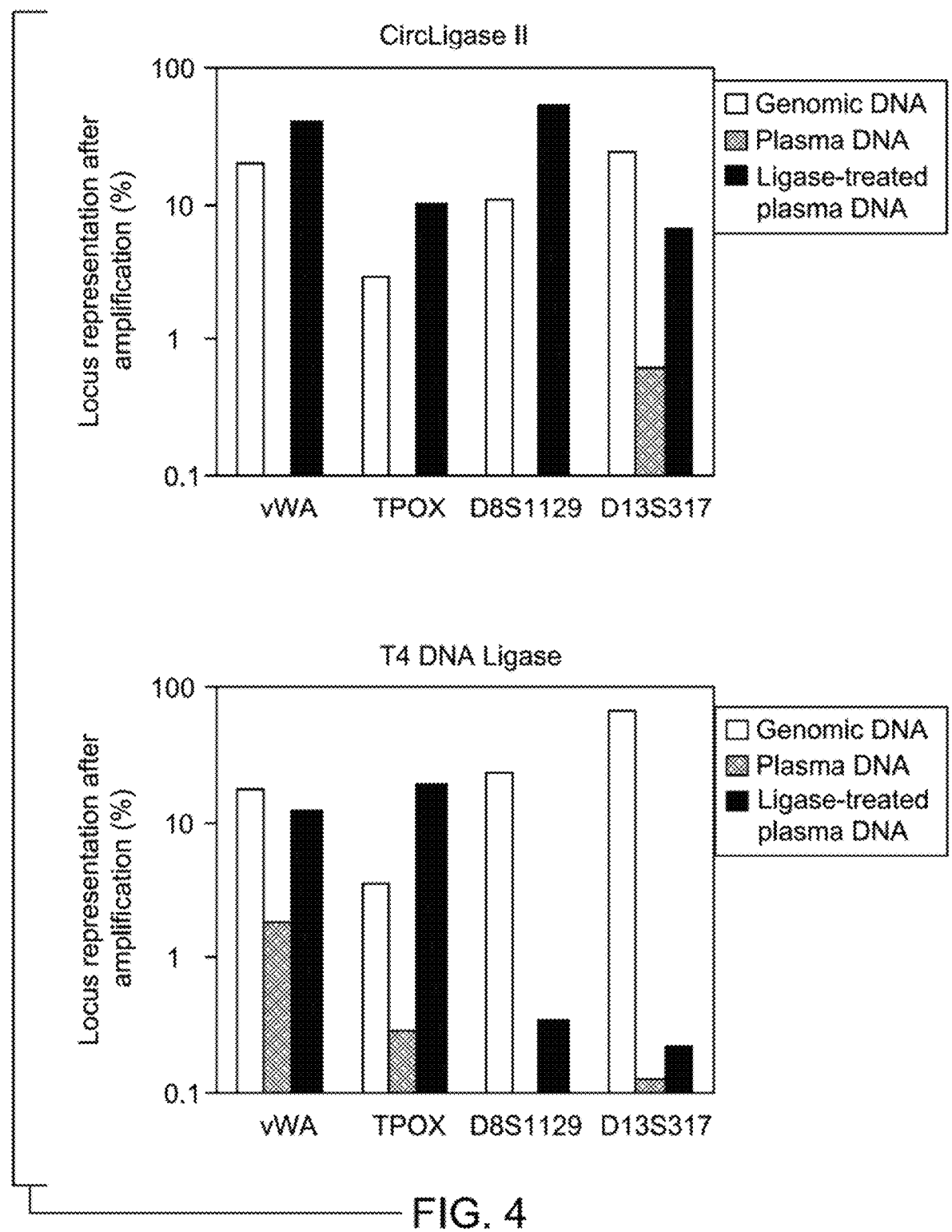
FIG. 4 illustrates the effectiveness of ligase-assisted whole-genome amplification for sensitive and balanced DNA amplification of four different CODIS loci.

Example 2: Analysis of Amplified Circulating Nucleic Acids from Blood Plasma by Ligase-Assisted Whole-Genome Amplification The amplified DNA generated in Example 1 was further analyzed by quantitative PCR using primers targeting four different CODI'S loci (vWA, TPOX, D8S1129, and D13S317) to sample the effectiveness of the ligase-assisted whole-genome amplification method for promoting sensitive and balanced DNA amplification. These DNA levels were compared with the values from unamplified DNA to determine the relative representation levels after amplification. As illustrated in FIG. 4, in both examples, the amplification of untreated plasma DNA led to sequence dropout or produced DNA that was highly under-represented at the tested loci. In contrast, including either CIRCLIGASE II or T4 DNA ligase in the method prevented the sequence dropout of the four loci and produced DNA that was more similar in representation to the amplified high molecular weight genomic DNA. In the example using CIRCLIGASE II as the single-stranded DNA ligase, out of 12 different CODIS loci tested by quantitative PCR (qPCR) using primers targeting 12 different CODIS loci, 11 were recovered after amplification, whereas only 4 were present in the amplified untreated plasma DNA (FIG. 5). In FIG. 5, the Ct values reported are an average of two replicates. PCR reactions where the Ct value was undetermined are marked by an "X".

Figure 6:
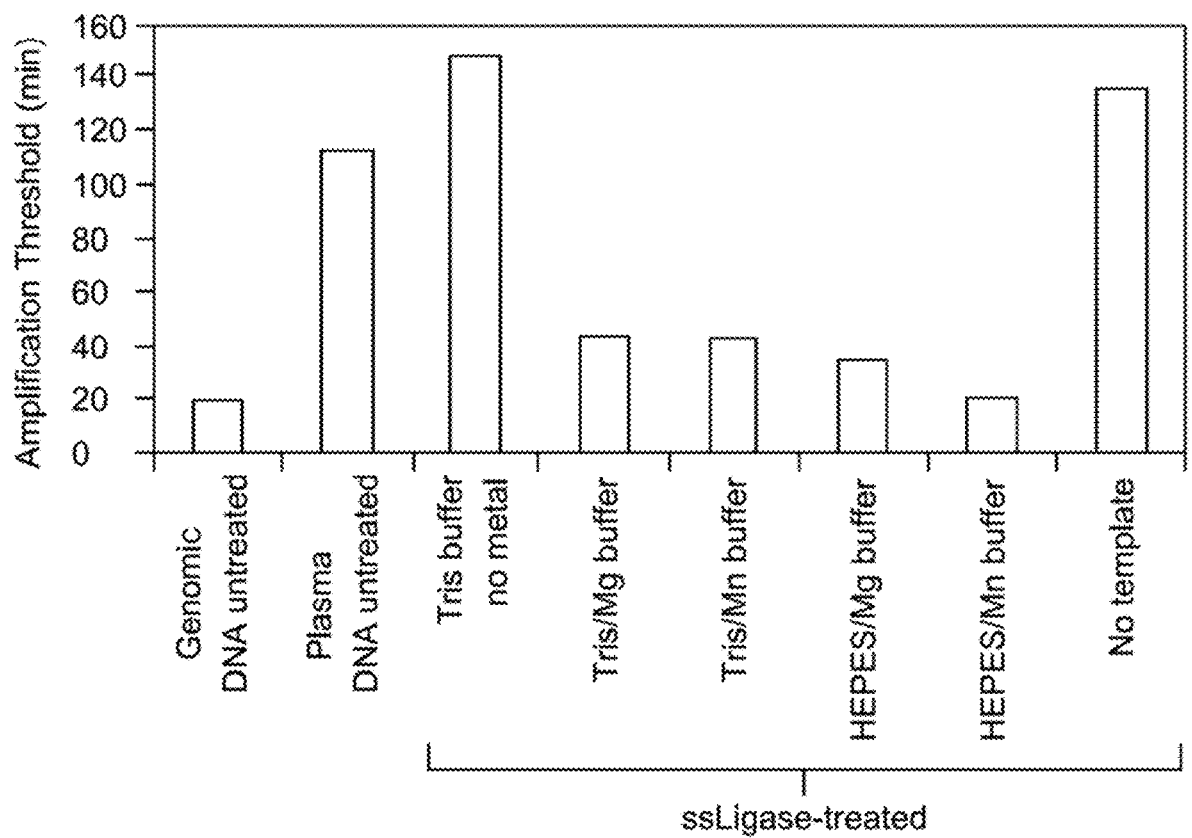
FIG. 6 illustrates the efficiencies of ligase-assisted whole-genome amplification in different reaction and buffer conditions.

Example 3: Optimization of Reaction Conditions for Ligase-Assisted Whole-Genome Amplification The ligase-assisted DNA amplification reaction was further optimized by optimizing the efficiency of ligation reaction of single stranded DNA molecule by TS2126 RNA ligase. The presence of metal ion was essential for the ligation reaction since eliminating manganese from the standard manufacturer recommended buffer reduced amplification rates to background levels. Untreated genomic DNA and untreated plasma DNA were compared with CIRCLIGASE II-treated plasma DNA samples using modified buffer conditions (FIG. 6). All buffer conditions contained 33 mM KOAc, 0.5 mM DTT, and IM betaine. Where indicated, buffers contained 33 mM Tris-acetate (pH 7.5) or 33 mM HEPES-KOH (pH 8.0) and additionally contained 2.5 mM $MgCl_2$ or 2.5 mM $MnCl_2$. Real-time amplification was performed by adding a small amount of SYBR green I to the amplification mixture and monitoring fluorescence increase over time in a Tecan plate reader. The amplification threshold is the time at which fluorescence rises above background levels (2000 RFU).

Comparison of amplification kinetics of ligase-assisted whole-genome amplification reactions (100 pg samples) is depicted in FIG. 6. Both magnesium and manganese promoted similar effects in the presence of the standard TRIS buffer, but it was observed that the combination of manganese and magnesium in the presence of HEPES buffer, pH 8.0 was most effective in promoting high amplification rates. HEPES buffer increased circularization efficiency of the plasma DNA in this reaction condition may be due reduced oxidation of the manganese cation in the HEPES buffer.

Figure 7:
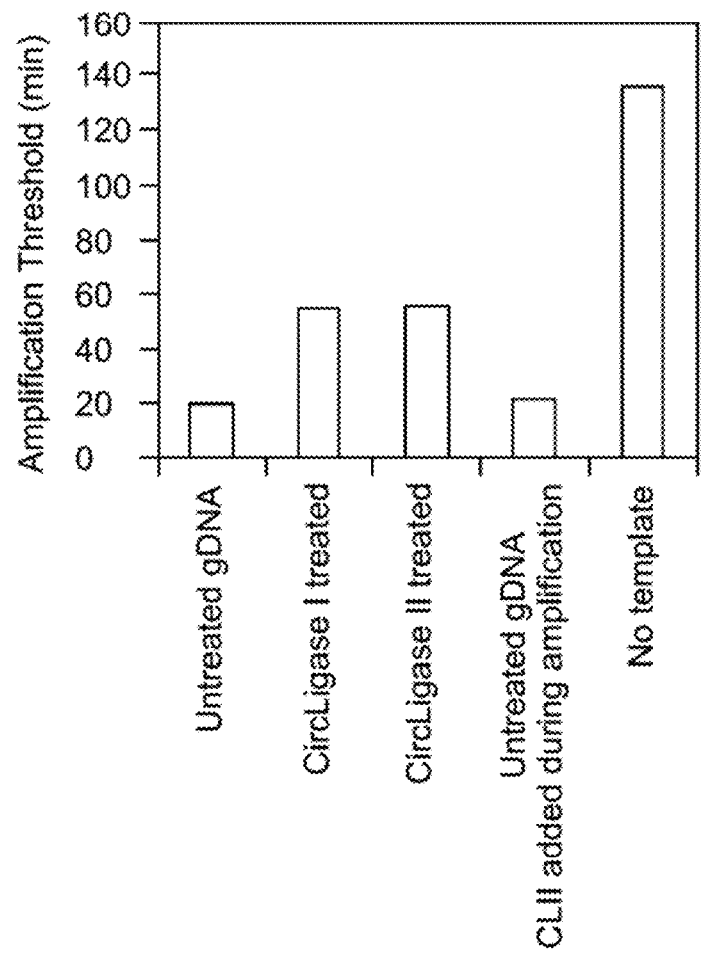
FIG. 7 illustrates the inhibition of amplification of high molecular weight genomic DNA in ligase-assisted whole-genome amplification.

Example 4: Inhibition of Amplification of High Molecular Weight Genomic DNA in Ligase-Assisted Whole-Genome Amplification The amplification kinetics of whole-genome amplification reactions of untreated genomic DNA was compared with CIRCLIGASE I and CIRCLIGASE II-treated genomic DNA samples (100 pg samples). The results are illustrated in FIG. 7. As depicted in FIG. 7, CIRCLIGASE treatment of genomic DNA produced an inhibitory effect on the amplification rate of high molecular weight genomic DNA (unlike the positive effects on plasma DNA). The inhibition was apparent for both CIRCLIGASE I and CIRCLIGASE II.

To investigate if Phi29-based amplification was inhibited by the ligase, untreated genomic DNA was amplified in the presence of active ligase. Real-time amplification was performed by adding a small amount of SYBR green I to the amplification mixture and monitoring fluorescence increase over time in a Tecan plate reader. Amplification threshold is the time at which fluorescence rises above background levels (2000 RFU). It was observed that the genomic DNA amplification inhibition was not an effect of active ligase being present during the amplification.

A preference for the amplification of circulating over high molecular weight genomic DNA might be an advantage for certain applications, as genomic DNA from blood cells often contaminates preparations of circulating nucleic acids, and is of less diagnostic value.

Example 5: Single-Tube Amplification of Fragmented DNA Employing Ligase-Assisted Whole-Genome Amplification—Effect of Phosphorylation of Circulating DNA Fragments with Kinase Prior to Intra-Molecular Ligation Phosphorylation of circulating DNA fragments with kinase allowed more sensitive detection of circulating DNA in blood plasma. A male-female plasma/blood mixing experiment was performed to establish that the library created from the input DNA treated with kinase was more representative, allowing for more sensitive detection of the DYS 14 male-specific marker (FIG. 10, 3/3 replicates, whereas only 1I3 was detected if phosphorylation was not done). 100 μL of blood/plasma mixtures were prepared as follows: 100A: 100% male plasma; 5A-C: male plasma spiked into female whole blood at 5% v/v; 1A-C: male plasma spiked into female whole blood at 1% v/v; and OA: 100% female blood. The plasma was separated from the blood cells by lateral flow through an MF1 membrane (Whatman) followed by collection onto a cellulose pad that was dried and stored overnight. The circulating DNA was then isolated from the cellulose pad by a modification of the Wako extractor SP kit (Wako Pure Chemical Industries), a standard sodium iodide/detergent based method. Approximately 1.8 ng of DNA was then treated with or without T4 polynucleotide kinase in the presence of GTP, manganese, and betaine and then treated with CIRCLIGASE II to circularize the single-stranded DNA fragments. DNA was then subjected to GenomiPhi whole-genome amplification (GE Healthcare) and products were analyzed by quantitative PCR to assess the detection of two markers: Dys14, which is a multi-copy gene located on the Y-chromosome and should be detectable from the male fraction only, and D16S539 which is an STR locus located on chromosome 16 and should be detectable from both male and female fractions. The reaction was performed in a single reaction vessel, without any intermediate purification or isolation steps in the workflow. This was achieved by performing the phosphorylation reaction at a relatively low concentration of GTP.

Figure 10:
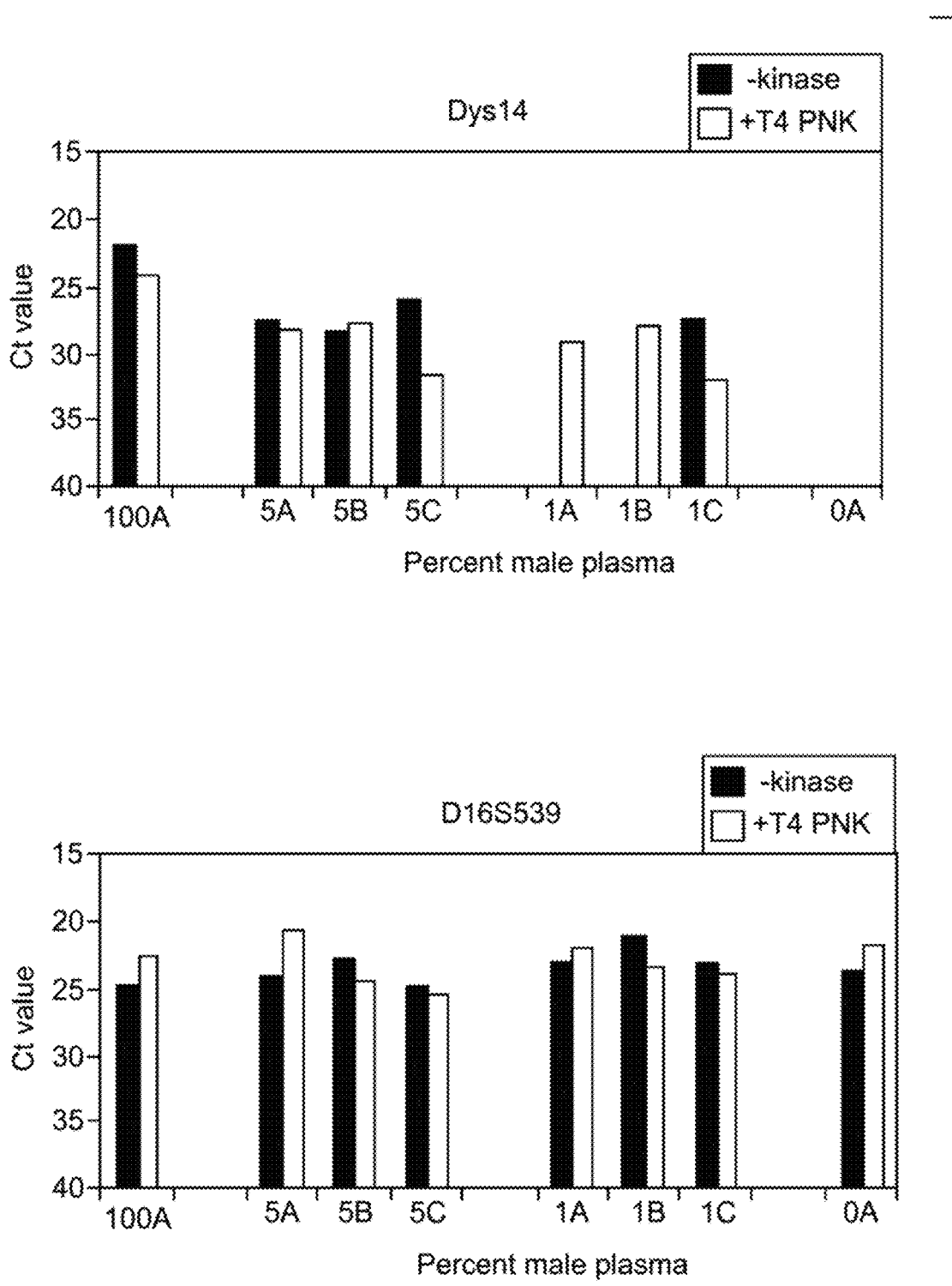
FIG. 10 illustrates a single-tube ligase-assisted amplification reaction using male-female plasma/blood, wherein DYS14 male-specific marker is detected using a library created from the input DNA.

FIG. 10 illustrates that inclusion of a kinase in the reaction allows the circularization and amplification of DNA fragments in a pool that do not contain a 5' phosphate, thereby creating a more representative library. This would include DNA fragments containing a 5' hydroxyl, which are specifically generated by DNase II digestion during cell death. Using a male-female plasma/blood mixing experiment, it is demonstrated that the library created from the input DNA treated with kinase was more representative, allowing for more sensitive detection of the DYS 14 male-specific marker (3/3 replicates, whereas only 1I3 was detected if phosphorylation was not done).

Figure 12:
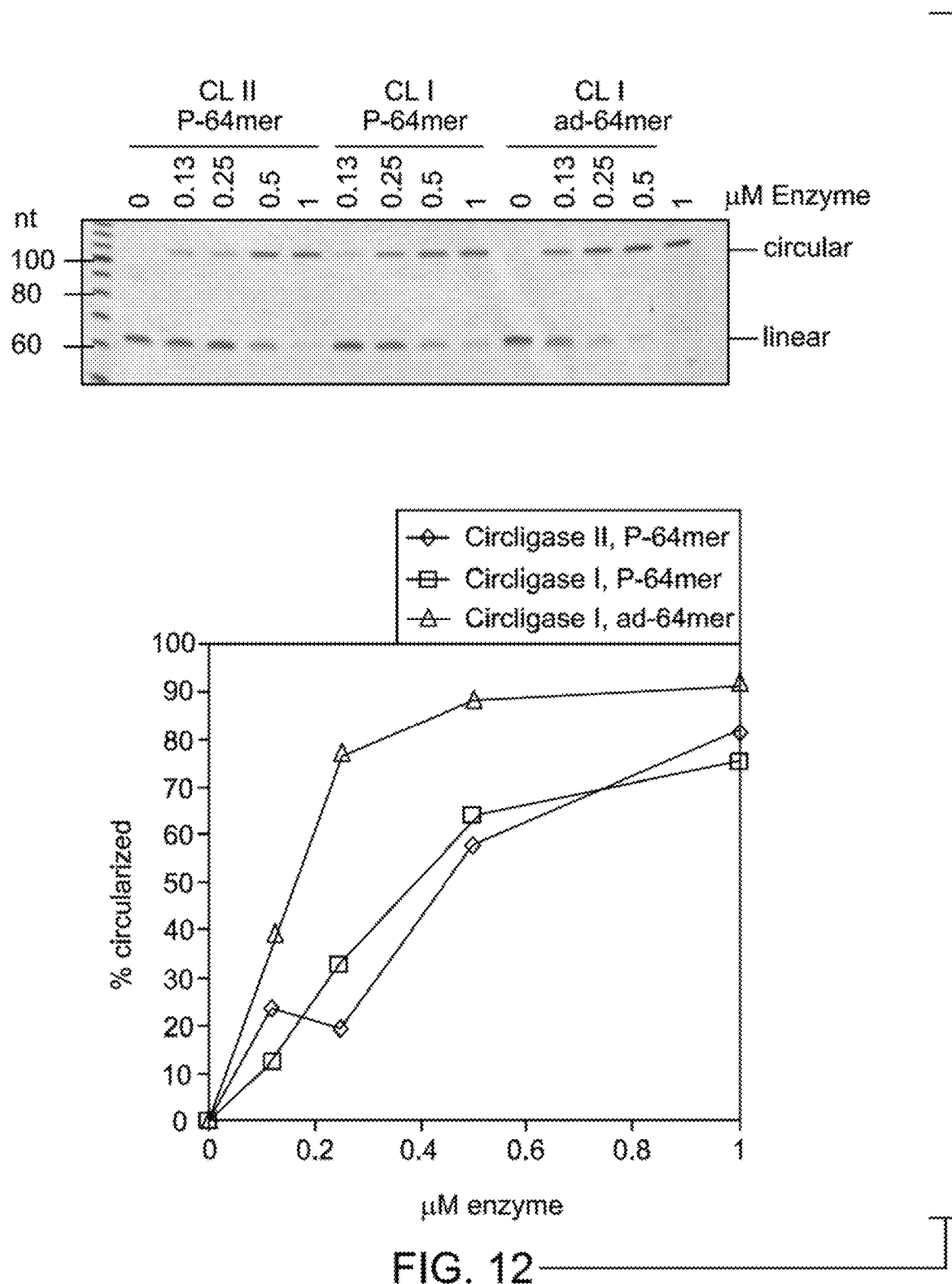
FIG. 12 illustrates the enhanced efficiency of circularization of a pre-adenylated DNA sequence using a substantially non-adenylated ligase.

Example 6: Effect of Pre-Adenylation of Fragmented DNA Prior to Circularization Reaction The efficiency of circularization of a small DNA fragment that is either phosphorylated or pre-adenylated in 40 minutes is assessed with different amounts of CIRCLIGASE enzyme. 2.5 pmol of a 64-mer oligonucleotide containing either a phosphate group or an adenylation at the 5' position was treated with increasing amounts of CIRCLIGASE I or CIRCLIGASE II for 40 minutes at 60° C. The percent circularization was determined by scanning the intensity of the bands at the linear and circular positions. As depicted in FIG. 12, pre-adenlyation of fragmented DNA improved the ligation and amplification kinetics. In FIG. 12, P-64mer represents a 5'-phosphorylated 64-nt oligonucleotide; and ad-64 represents pre-adenylated 64-nt oligonucleotide. Pre-adenylated DNA was circularized more rapidly than the standard phosphorylated DNA. Further, the ligation enzyme, which has low degree of adenylation catalyzed the ligation of a molar excess of substrate indicating that the ligase has multiple opportunities to ligate the pre-adenylated DNA molecule, which increases ligation kinetics and potentially allows for increased circularization of more difficult templates.

Figure 13:
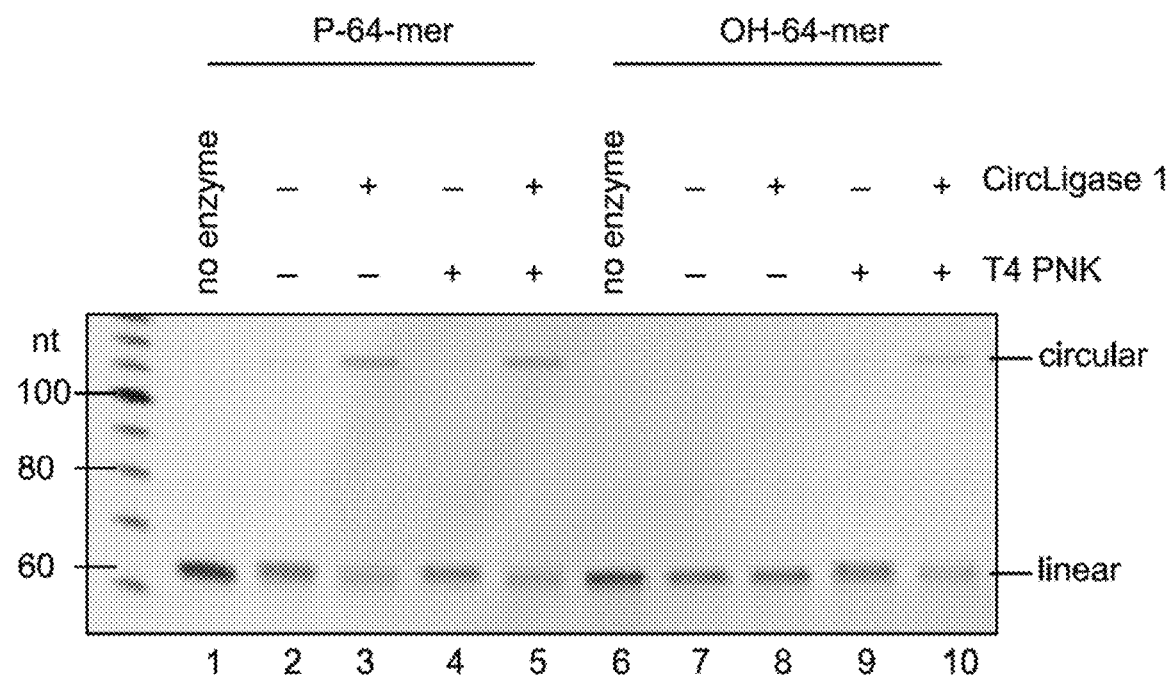
FIG. 13 illustrates the enhanced efficiency of ligase-assisted whole-genome amplification when the target DNA sequence was pre-adenylated and when the ligation was performed using a non-adenylated ligase.

Example 7: Circularization of 5'-Phosphate and 5'-Hydroxyl-Containing Oligonucleotides Using the Pre-Adenylation Workflow Reactions containing 5 pmol of a 64-mer oligonucleotide with either a phosphate group or a hydroxyl group at the 5' position were treated with 1.25 U of T4 polynucleotide kinase at 37° C. where indicated. Following incubation with 25 pmol Mth RNA ligase at 65° C., reactions were treated with 0.25 units of shrimp alkaline phosphatase. Since Mth RNA ligase is very sensitive to ATP concentration, at standard 100 μM ATP concentration, Mth RNA ligase almost exclusively adenylate DNA ends. No intra-molecular ligation happens by Mth RNA ligase at this ATP concentration. Enzymes were heat-inactivated after each incubation. Finally, reactions were treated with 50 units of CIRCLIGASE I where indicated and incubated for 60 minutes at 60° C. The percent circularization was determined by scanning the intensity of the bands at the linear and circular positions (FIG. 13). P-64mer represents a 5'-phosphorylated 64-nt oligonucleotide and ad-64mer represents a pre-adenylated 64-nt oligonucleotide.

Figure 11:
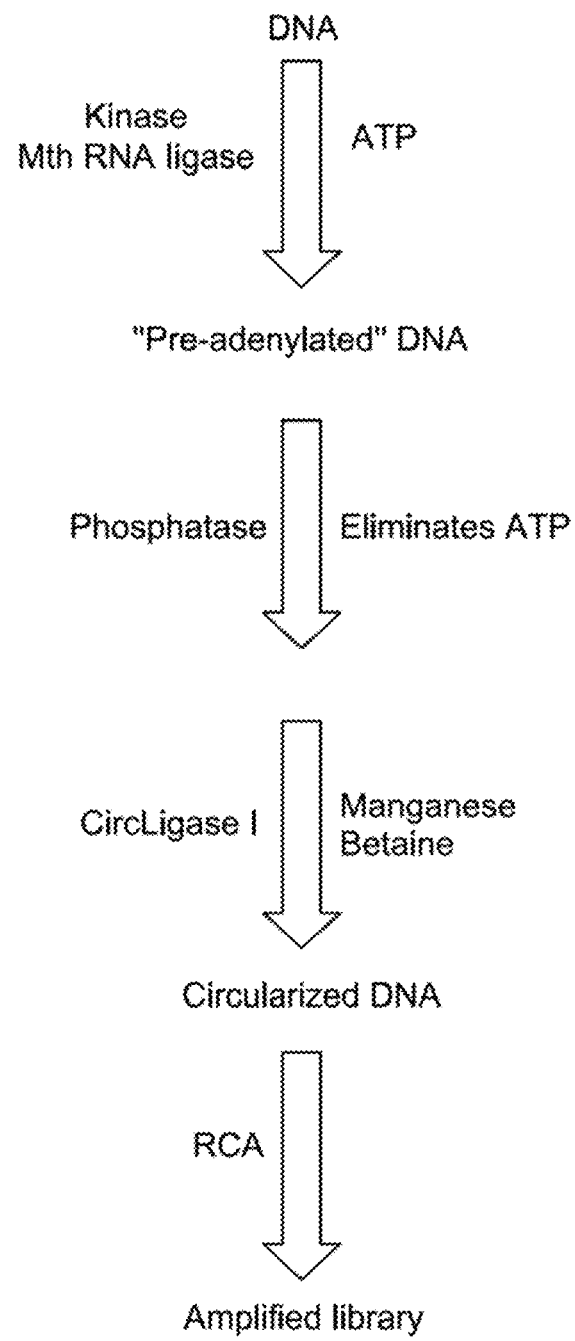
FIG. 11 illustrates a schematic representation of phosphorylation and pre-adenlyation of fragmented DNA followed by ligation using a substantially non-adenylated ligase.

FIG. 11 shows a "single-tube" pre-adenylation workflow in which linear oligonucleotides containing a 5'-phosphate or a 5'-hydroxyl group are converted to circular forms. In this «single-tube" process substrates are successively treated with polynucleotide kinase, Mth RNA ligase, shrimp alkaline phosphatase, and CIRCLIGASE I without any intermediate purification steps.

Example 8: Kinetics of Whole-Genome Amplification of Fragmented Nucleic Acid from Blood Plasma Plasma DNA was isolated from an apparently healthy individual using the Wako DNA extractor SP kit (Wako Pure Chemical Industries). 1 ng of purified plasma DNA was heated at 95° C. to denature the template. The denatured, single-stranded DNA template was then treated with an RNA ligase (CIRCLIGASE II, Epicenter) to generate single-stranded DNA circles. For the ligation reaction, the plasma DNA was incubated with a ligation reaction mixture (6 μL) containing 50 mM HEPES, pH 8.0, 66 mM KOAc, 0.5 mM DTT, 1 M betaine, and 30 U CIRCLIGASE II (Epicentre) at 60° C. for 2 hours. The ligase was subsequently heat-inactivated by incubating the reaction mixture at 80° C. for 10 minutes. The single-stranded DNA circles were then subjected to whole-genome amplification using random-primed rolling circle whole genome amplification employing a phi29 DNA polymerase. The single-stranded DNA circles were amplified in the same reaction vessel, without intervening purification of the DNA by adjusting the ligation reaction mixture to the following conditions: 20 mM $MgCl_2$, 1 mM TCEP, 0.01% Tween-20, 2.5% PEG-8000, 40 μM AT random hexamer primer mixture, 20 ng/L Phi29 polymerase and 50 mM HEPES (pH 8.0) to a final volume of 20 µL. The amplification reaction mixture was incubated at 30° C. for 10 hours, followed by heat-inactivation of polymerase at 65° C. for 20 minutes. Real-time amplification was performed by adding a small amount of SYBR green I to the amplification mixture and monitoring the fluorescence signal increase over time in a Tecan plate reader (Tecan SNiPer, Amersham-Pharmacia Biotech). The amplification was performed using the random primer mixture having a sequence+N+N(at N)(at N)(at N)*N (AT random hexamer) where the "at N" represents a random mixture containing 2-amino dA, 2-thio-dT, normal G and normal C.

For comparison, an equivalent concentration of plasma DNA amplified with standard random hexamer (NNNN*N*N) and a sample without DNA template (No template control) using the same protocol as described above. The amplification reactions performed with AT random hexamer primer mixture surprisingly showed faster kinetics and produced a significantly higher amplified product DNA yield compared to standard random hexamer, as shown in FIG. 14. DNA yield for amplification using AT random hexamer is 2.25 µg in comparison to the DNA yield of 0.84 µg using standard random hexamer. The DNA yield is zero for "no template control" (NTC) reaction. As depicted in FIG. 14, when the plasma DNA was ligated and converted to single-stranded DNA circles using CIRCLIGASE II, rapid amplification kinetics were achieved when a random primer comprising a modified nucleotide such as AT random hexamer is used. (FIG. 3). The single-tube ligation and amplification reactions contain carryover components from the DNA ligation reaction including betaine, potassium acetate, and manganese, which are typically known to have inhibitory effect on amplification. However, when the reaction was performed in presence of AT random hexamer, which comprises modified nucleotides, this inhibitory effect on amplification was surprisingly minimal. The relative increase in amplification kinetics as illustrated in FIG. 14 indicates the effectiveness of a random primer mixture comprising at least one modified nucleotide in promoting the rolling circle amplification reaction subsequent to the intramolecular ligation of the single-stranded DNA template in the same reaction vessel without any intervening isolation or purification steps.

Figure 15:
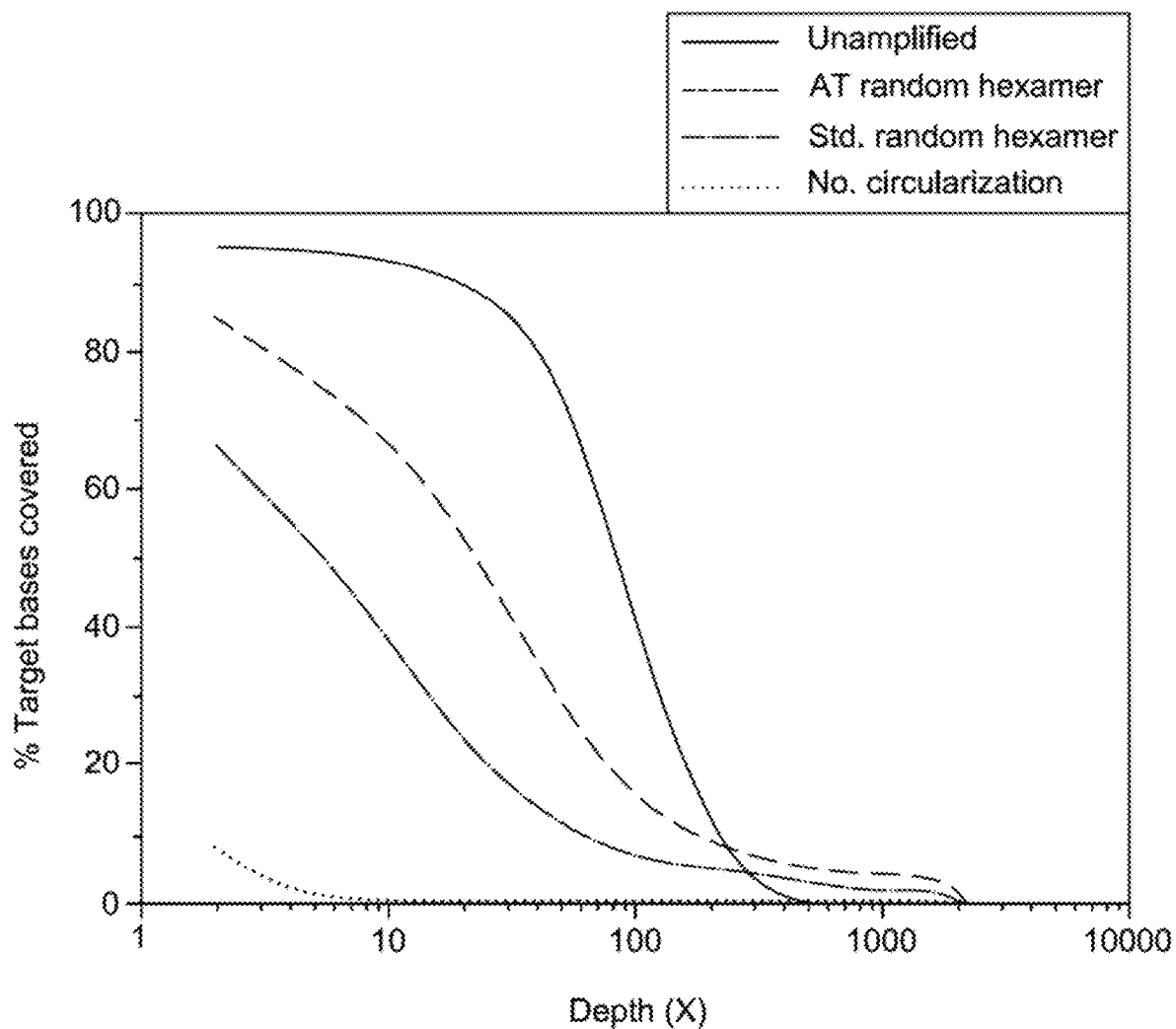
FIG. 15 illustrates qualitative analysis of amplified DNA with respect to coverage depth and uniformity levels.

Example 9: Sequence Analysis of Amplified Nucleic Acids from Blood Plasma by Ligase-Assisted Whole-Genome Amplification The amplified DNA product generated in Example 8 was purified by ethanol precipitation and subjected to sequencing reaction to determine the quality of the ligase-assisted whole-genome amplification method using AT random hexamer primer. The sequencing was performed employing Ton Ampliseq Comprehensive Cancer Panel single-end targeted sequencing using the Ion Torrent PGM with 318 chips and 200 bp read lengths. As illustrated in FIG. 15, the amplified DNA product using the AT random hexamers is of higher quality than the DNA amplified using standard random bexamers. The percentage of bases recovered for DNA amplified using the AT hexamers is closer to those from bulk unamplified plasma DNA. The coverage depth and uniformity levels of DNA amplified using the AT hexamers are closer to those from bulk unamplified plasma DNA, as shown in Table 2.

TABLE 1

Characterization of amplified DNA using AT-hexamer compared to standard random hexamer control

| Sample | Input Quantity (ng) | Read on target (%) | Avg. coverage depth (X) | Coverage standard deviation | Coverage uniformity (%) |
|---|---|---|---|---|---|
| Unamplified | 40 | 92.38 | 110.27 | 88.94 | 92.34 |
| AT Random hexamer | 1 | 97.42 | 156.39 | 560.09 | 46.15 |
| Standard random hexamer | 1 | 95.79 | 76.8 | 294.48 | 37.99 |
| No circularization (one step reaction) | 1 | 96.1 | 442.77 | 5603.4 | 1.66 |

Figure 16:
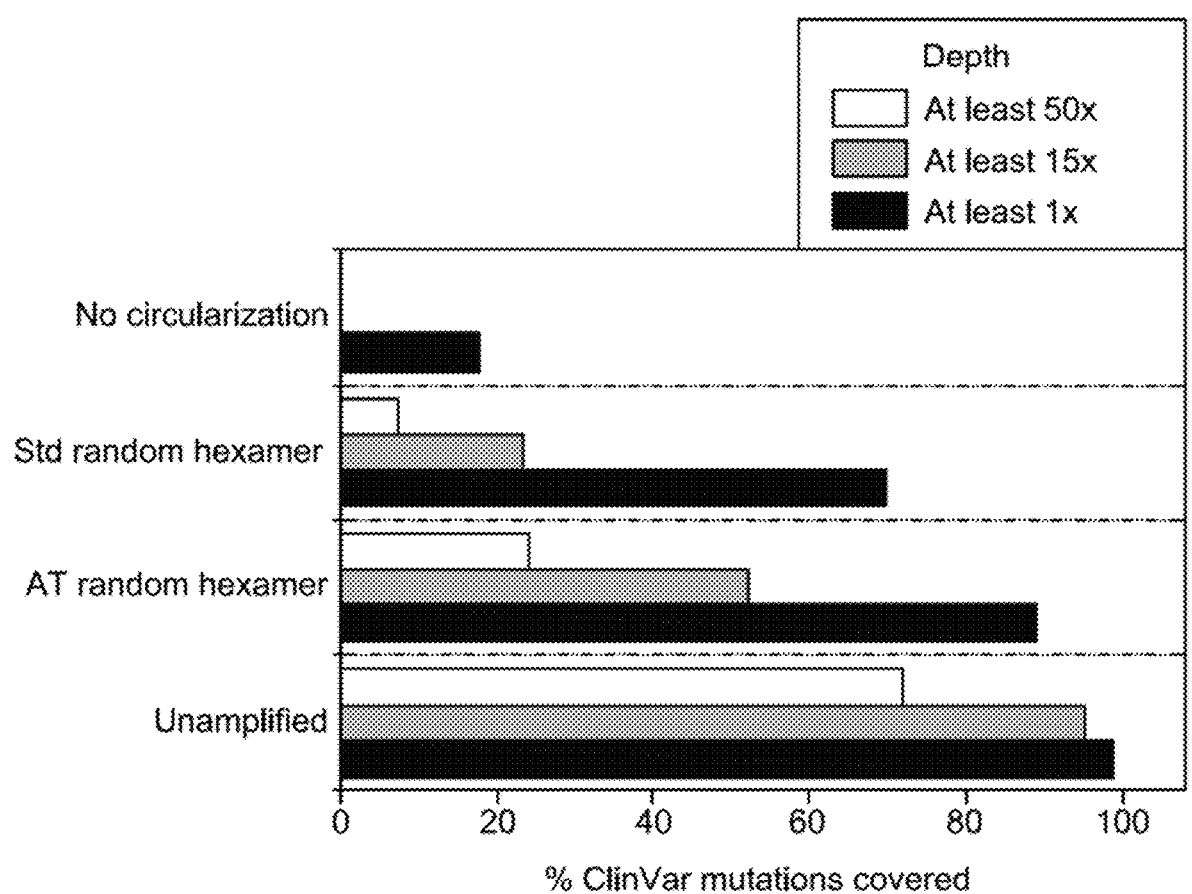
FIG. 16 illustrates the overall coverage and uniformity observed throughout the target sequence region using the AT hexamers.

The higher overall coverage and uniformity observed throughout the target sequence region using the AT random hexamers also provided higher coverage depth at regions with clinically relevant single nucleotide polymorphisms (SNPs) as measured at known ClinVar mutation sites (FIG. 16, wherein the labeling denotes average depth of coverage, lx depth, 15× depth and so on). The figure shows that at all cut-off levels, the AT primers cover a greater percentage of ClinVar mutation regions than the random primers In contrast, in one-step reactions in which the plasma DNA is directly amplified without a circularization step, the sequence coverage was extremely poor, with variable coverage depths at these regions and poor coverage at ClinVar mutation sites.

Example 10: Single-Tube FFPE Tissue Extraction, DNA Circularization, Repair, and Whole Genome Amplification for Targeted Re-Sequencing Deparaffinization of FFPE tissue slides was performed by incubating the FFPE tissue slides in an oven at 65° C. for an hour. The deparaffinized slides were washed twice using HISTOCHOICE Clean Agent (AMRESCO, cat # H103) for 5 minutes. The slides were washed successively with 100% ethanol (twice, 5 minutes each time), 75% ethanol (once, 5 minutes) and 50% ethanol (once, 5 minutes). The slides were then rinsed with nuclease-free water and air-dried. The antigens were retrieved from the slides using Citrate-TRIS antigen retrieval (AR) buffers. The Citrate-AR (pH 6.0) and TRIS-AR buffer (pH 8.5) were pre-warmed at 70° C. for 20 minutes. The slides were placed in a jar containing pre-warmed Citrate-AR and the jar was placed in a pressure cooker at 110° C. for 4 minutes followed by 75° C. for 20 minutes. The sides were then transferred to pre-warmed TRIS-AR buffer and kept for 20 minutes. The jar was cooled at room temperature for 10 minutes and the slides were washed briefly with water and then air dried. The FFTE tissue was then digested using proteinase K. For digestion, 0.6 µL of 2 mg/mL proteinase K digest solution was used for 1 mm² areas of tissue (e.g., for a 4 mm×6 mm tissue section, about 15 µL of proteinase K digest solution was used). The proteinase K digest solution was prepared by mixing L of 20 mg/mL proteinase (Invitrogen # AM2548) with 5 µL of tissue digestion buffer (30 mM HEPES (pH 8.0), 1 mM EDTA, 0.5% SOS and 0.01% Tween-20). First, 0.5 µL of the proteinase K digest solution was added to the slide to wet the tissue. Using an ethanol wiped razor blade; the tissue was scraped and transferred to 0.2 mL tube. The rest of the 2 mg/mL Proteinase K digest solution was then added to the tube and was incubated at 50° C. for 2 hours or more until the slurry turned clear. The slurry was cooled to room temperature and 2 μL of crude extraction was kept aside for DNA concentration measurement (QUANT-IT DNA Assay Kit, high sensitivity (Invitrogen # Q-33120))

To inactivate the digestion mixture, 5 μL of crude extracted (containing 40 ng of DNA) is treated with a proteinase K inhibitor (0.6 μL of 5 mM Proteinase K inhibitor (EMD Millipore #539470), 3.3 μL 9.1% alpha-cyclodextrin, (Sigma # C4680)). The sample is then processed in 3 different combinations.

REV 10 protocol—To the extract was added 1.1 μL of 5 M betaine, 1.1 μL of 10× Circularization buffer (350 mM HEPES (pH 8.0), 25 mM $MnCl_2$, 660 mM KOAc, 5 mM DTT, and 0.03% Tween-20) and up to 10.56 μL of nuclease-free water (Total volume of 11 μL). The mixture was incubated at room temperature for 10 minutes. Subsequently the reaction mixture was heated to about 95° C. for 3 minutes followed by snap cooling on ice. To this was added 0.44 μL of CIRCLIGASE II (Epicentre # CL9025K) to a final reaction volume of 11 μL. The reaction mixture was incubated in thermocyler at 60° C. for 8 hours followed by at 80° C. for 10 minutes to inactivate enzyme.

REV11 protocol—To the extract was added the repair reaction components by adding 1.1 μL of 10× Repair buffer (0.03% Tween-20, 100 mM $MgCl_2$, 6 mM DTT), 0.77 μL repair/damage elimination mix (0.6 μL UDG (5 U/μL), 0.3 μL Fpg (8 U/μL), 0.15 μL Endo IV (10 U/μL) (New England Biolabs)) and nuclease-free water to have a final volume of 11 μL. The reaction mixture was incubated in thermocycler at 37° C. for 30 minutes followed by 85° C. for 15 minutes to inactivate enzymes. To this was added 1.5 μL of 5 M betaine, 1.5 μL of 10× Circularization buffer (350 mM HEPES (pH 8.0), 25 mM $MnCl_2$, 660 mM KOAc, 5 mM DTT, and 0.03% Tween-20) and nuclease-free water (Total volume of 14.4 μL). The reaction mixture was heated to about 95° C. for 3 minutes followed by snap cooling on ice. To this was added 0.6 μL of CIRCLIGASE II (Epicentre # CL9025K) to a final reaction volume of 15 μL. The reaction mixture was incubated in heat block at 60° C. for 8 hours followed by at 80° C. for 10 minutes to inactivate enzyme.

REV 12 protocol—To be extract was added 1.1 μL of 5 M betaine, 1.1 μL of 10× Circularization buffer (350 mM HEPES (pH 8.0), 25 mM $MnCl_2$, 660 mM KOAc, 5 mM DTT, and 0.03% Tween-20) and nuclease-free water (Total volume of 10.56 μL). The mixture was incubated at room temperature for 10 minutes. Subsequently the reaction mixture was heated to about 95° C. for 3 minutes followed by snap cooling on ice. To this was added 0.44 μL of CIRCLIGASE II (Epicentre # CL9025K) to a final reaction volume of 11 μL. The reaction mixture was incubated in thermocyler at 60° C. for 8 hours followed by at 80° C. for 10 minutes to inactivate enzyme. The entire circularization mix (11 μL) was used for the repair/damage elimination reaction by adding 1.5 μL of 10× Repair buffer (0.03% Tween-20, 100 mM $MgCl_2$, 6 mM DTT), 1.05 μL repair mix (0.6 μL UDG (5 U/μL), 0.3 μL Fpg (8 U/μL), 0.15 μL Endo IV (10 U/μL) (New England Biolabs)) and 1.45 μL of nuclease-free water to have a final volume of 15 μL. The reaction mixture was incubated in thermocycler at 37° C. for 30 minutes followed by at 85° C. for 15 minutes to inactivate enzymes.

For DNA amplification, a cleaning reaction master mix was assembled my mixing 20 μL of 3×Pbi29 buffer (114 mM HEPES (pH 8.0), 120 μM AT primer mixture 0.021% Tween-20, 54.6 mM $MgCl_2$, 3 mM TCEP, 7.5 mM KOAc and 7.5% PEG-8000), 0.3 μL of 1:100 SYBR Green I*(Life Tech S-7563), 1.2 μL of Phi29 polymerase (1 mg/mL, GE Healthcare), 21.1 μL of nuclease-free water to a final volume of 42.6 μL. The cleaning reaction master mix was incubated at 30° C. for 1 hour and was held at 4° C. until ready for use. The amplification reaction was initiated by adding 2.4 μL of 10 mM dNTPs solution to the cleaning reaction. Immediately the entire cleaned reaction mix was added to the 15 μL repaired mix for a final reaction volume of 60 μL. This was incubated at 30° C. for 8-16 hours followed by heat-inactivation of the polymerase at 65° C. for 15 minutes. In a real time setup the data was collected every 10 minutes.

The whole genome amplification products were purified by manufacturer's instruction for purification (SURE-CLEAN PLUS, Bioline). Briefly, 60 μL of SURECLEAN PLUS was added to 60 μL of WGA product and mix thoroughly. This was incubated for 30 minutes at room temperature and centrifuged at maximum speed in a bench-top centrifuge for 30 minutes. The supernatant was removed by aspiration. 120 μL freshly made 70% ethanol was added and vortexed for 10 seconds and centrifuged at maximum speed for 15 minutes. The supernatant was removed carefully. The washing steps were repeated once, then air dried to ensure complete removal of ethanol. The dried pellets were re-suspended in 30 μL of 10 mM Tris-HCl (pH 8). 2 L of purified WGA products was used for DNA concentration measurement (QUANT-IT dsDNA Broad-Range Assay Kit, Invitrogen # Q-33130). The expected yield was about 3 μg.

Figure 17:
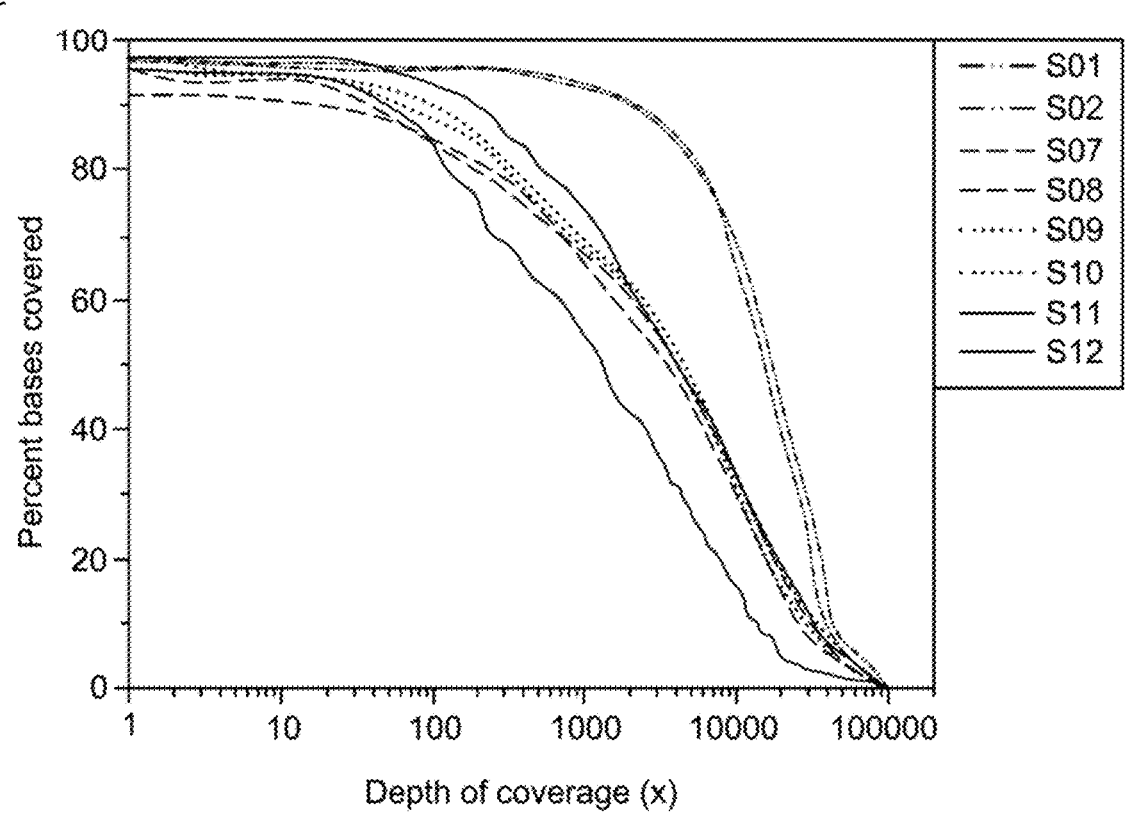
FIG. 17 illustrates the depth of coverage when uracil DNA glycosylases (UDG) and formamidopyrimidine-DNA glycosylase (Fpg) was employed to repair/eliminate damage from the single stranded DNA prior to the generation of single-stranded DNA circle or to repair/eliminate damage from the generated single-stranded DNA circles, or when no DNA damage repair/elimination was performed.

DNA samples were analyzed using next generation sequencing on the MiSeq platform (Illumina). The TruSeq Amplicon-Cancer Panel (TSACP) (Illumina), which is a highly multiplexed targeted re-sequencing assay for detecting somatic mutations, was used according to the manufacturers recommendations. 250 ng of DNA from freshly frozen tissue was used as a positive control, and 1,000 ng of rolling circle amplified whole genome DNA from 40 ng of FFPE DNA resulting from the REV10, REV11, and REV12 protocol, all in duplicate, were used in the sequencing workflow. From these sequencing reactions, depth of coverage, sequence target uniformity, and mutation statistics were determined. As illustrated in FIG. 17, FIG. 18, and FIG. 19, the REV10, 11, and 12 protocols provide excellent depth of coverage and uniformity of coverage. However, the REV12 protocol in which the DNA repair/DNA damage removal step was performed after the long DNA circularization step had an improved positive predictive value and increased sensitivity compared to the REV10 and REV11 protocols (FIG. 19).

The claimed invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention described herein. While only certain features of the claimed invention have been illustrated and described herein, it is to be understood that one skilled in the art, given the benefit of this disclosure, will be able to identify, select, optimize or modify suitable conditions/parameters for using the methods in accordance with the principles of the present invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the true spirit of the invention.

Further, all changes that come within the meaning and range of equivalency of the claims are intended to be embraced therein.

The invention claimed is:

1. A method for nucleic acid amplification, the method comprising:
   (a) ligating a linear chromosomal DNA to generate a single-stranded DNA circle; and
   (b) amplifying the single-stranded DNA circle via rolling circle amplification using a random primer mixture to form an amplified DNA product,
   wherein the random primer mixture comprises 2-amino-deoxyadenosine and 2-thio-deoxythymidine nucleotide analogs, and
   wherein all the steps of the method are performed in a single reaction vessel without any intervening isolation or purification steps.

2. The method of claim 1, wherein the random primer mixture comprises selective binding complementary oligonucleotides.

3. The method of claim 1, wherein the random primer mixture further comprises a phosphorothioate modified nucleotide, a LNA nucleotide, or combinations thereof.

4. The method of claim 1, wherein the linear chromosomal DNA is selected from the group consisting of a cell-free circulating DNA, a DNA isolated from a formalin fixed paraffin-embedded sample, a forensic DNA sample that has been exposed to environmental conditions, an ancient DNA sample, and combinations thereof.

5. The method of claim 1, wherein the linear chromosomal DNA is a fragmented DNA.

6. The method of claim 1, further comprising denaturing the linear chromosomal DNA to a single-stranded DNA prior to step (a), if the linear chromosomal DNA is in double-stranded form.

7. The method of claim 1, wherein the ligase is selected from the group consisting of a TS2126 RNA ligase, a T4 RNA ligase, a T4 DNA ligase, a T3 DNA ligase, an *E. coli* DNA ligase, and combinations thereof.

8. The method of claim 7, wherein the ligase is a pre-adenylated ligase.

9. The method of claim 8, wherein the pre-adenylated ligase is a pre-adenylated TS2 126 RNA ligase.

10. The method of claim 1, wherein the generation of the single-stranded DNA circle is performed in the absence of adenosine triphosphate or deoxyadenosine triphosphate.

11. The method of claim 1, wherein steps (a) to (b) are performed in a sequential manner in the single reaction vessel.

12. The method of claim 1, further comprising treating the linear chromosomal DNA with a polynucleotide kinase in the presence of a phosphate donor to generate a ligatable DNA sequence having a phosphate group at a 5' terminal end and a hydroxyl group at a 3' terminal end prior to incubating the linear chromosomal DNA with the ligase.

13. The method of claim 12, wherein the linear chromosomal DNA is treated with the polynucleotide kinase in the presence of a phosphate donor other than adenosine triphosphate or deoxyadenosine triphosphate.

14. The method of claim 1, further comprising sequencing the amplified DNA product.

15. The method of claim 6, further comprising treating the single stranded DNA circles prior to step (b) to modify any damaged nucleobases.

16. The method of claim 1, wherein the amplification is a whole genome amplification.

* * * * *